US010808241B2

(12) United States Patent
Abysalh et al.

(10) Patent No.: US 10,808,241 B2
(45) Date of Patent: Oct. 20, 2020

(54) METHODS FOR PURIFICATION OF MESSENGER RNA

(71) Applicant: Translate Bio, Inc., Cambridge, MA (US)

(72) Inventors: Jonathan Abysalh, Cambridge, MA (US); Daniel Crawford, Cambridge, MA (US); Frank DeRosa, Cambridge, MA (US); Shrirang Karve, Cambridge, MA (US); Anusha Dias, Cambridge, MA (US); Michael Heartlein, Cambridge, MA (US)

(73) Assignee: Translate Bio, Inc., Lexington, MA (US)

( * ) Notice: Subject to any disclaimer, the term of this patent is extended or adjusted under 35 U.S.C. 154(b) by 0 days.

(21) Appl. No.: 15/906,864

(22) Filed: Feb. 27, 2018

(65) Prior Publication Data

US 2018/0251755 A1 Sep. 6, 2018

Related U.S. Application Data

(60) Provisional application No. 62/463,998, filed on Feb. 27, 2017.

(51) Int. Cl.
*C12N 15/10* (2006.01)
*B01L 3/00* (2006.01)
*C12Q 1/6806* (2018.01)

(52) U.S. Cl.
CPC .... *C12N 15/1017* (2013.01); *B01L 3/502753* (2013.01); *C12Q 1/6806* (2013.01); *B01L 2200/028* (2013.01); *B01L 2200/16* (2013.01); *B01L 2300/0681* (2013.01); *B01L 2400/0409* (2013.01); *C12Q 2523/113* (2013.01); *C12Q 2523/308* (2013.01); *C12Y 201/03003* (2013.01)

(58) Field of Classification Search
CPC .......... C12N 15/1017; B01L 3/502753; C12Q 1/6806
See application file for complete search history.

(56) References Cited

U.S. PATENT DOCUMENTS

| | | | |
|---|---|---|---|
| 5,234,809 A | 8/1993 | Boom et al. | |
| 9,850,269 B2 * | 12/2017 | DeRosa | C07H 21/02 |
| 10,155,785 B2 * | 12/2018 | DeRosa | C07H 21/02 |
| 2004/0219534 A1 | 11/2004 | Belly et al. | |
| 2006/0127790 A1 * | 6/2006 | Matsumura | G03G 9/0804 430/109.4 |
| 2013/0059008 A1 | 3/2013 | Atkinson et al. | |

(Continued)

FOREIGN PATENT DOCUMENTS

WO WO2014/140211 A1 9/2014

OTHER PUBLICATIONS

Paleologue et al, Selective Silver-Staining Methods for RNA and Proteins in the Same Polyacrylamide Gels, 1988, Analytical Biochemistry, 169, 234-238. (Year: 1988).*

(Continued)

*Primary Examiner* — Narayan K Bhat
(74) *Attorney, Agent, or Firm* — Proskauer Rose LLP; Fangli Chen; Julio J. Mendez

(57) ABSTRACT

The present invention relates, in part, to methods for large-scale purification of mRNA. The method includes, at least, steps of forming an mRNA slurry, stirring the slurry, and vacuum or pressure filtering the slurry.

21 Claims, 2 Drawing Sheets

(56) References Cited

U.S. PATENT DOCUMENTS

| | | | |
|---|---|---|---|
| 2014/0205579 A1* | 7/2014 | Davis | A61K 48/005 424/93.21 |
| 2014/0294940 A1* | 10/2014 | Guild | A61K 31/7105 424/450 |
| 2015/0376220 A1* | 12/2015 | DeRosa | C07H 21/02 536/23.1 |

OTHER PUBLICATIONS

Farrell, R. E. et al., "Chapter 5: RNA Isolation Strategies", RNA Methodologies (Third Edition). A Laboratory Guide for Isolation and Characteriza, Jan. 1, 2005, pp. 67-113.

Kingston, R. E. et al., "Chapter 4—Unit 4.2: Guanidine methods for total RNA", Current Protocols in Molecular Biology, vol. 36, No. 1, (Oct. 1996), pp. 4.2.1-4.2.9.

International Preliminary Report on Patentability for International Patent Application No. PCT/US18/19954, dated Aug. 27, 2019 (7 pages).

International Search Report and Written Opinion for International Patent Application No. PCT/US18/19954, dated Aug. 30, 2018 (11 pages).

* cited by examiner

METHODS FOR PURIFICATION OF MESSENGER RNA

CROSS-REFERENCE TO RELATED APPLICATIONS

The present application claims benefit of U.S. Provisional Application No. 62/463,998, filed Feb. 27, 2017, which is hereby incorporated by reference in its entirety.

BACKGROUND OF THE INVENTION

Messenger RNA (mRNA) therapeutics are promising new therapeutic agents; for example, mRNA replacement therapeutics can be alternatives to traditional protein replacement therapies. In an mRNA replacement therapeutic, an intact mRNA encoding a specific protein sequence is delivered to a target cell and is translated into an intact protein by the cell's native translational machinery. mRNA for such therapeutics typically are synthesized using in vitro transcription systems with enzymes such as RNA polymerases transcribing mRNA from template plasmid DNA, along with or followed by addition of a 5'-cap and 3'-polyadenylation. The result of such reactions is a composition which includes full-length mRNA and various undesirable contaminants, e.g., enzymes, proteins, salts, buffers, and non-mRNA nucleic acids, which are typically omitted to provide a clean and homogeneous mRNA that is usable in an mRNA replacement therapeutic.

Traditionally, mRNA is purified from in vitro transcription reactions by either commercially-available silica-based column systems, such as the Qiagen RNeasy® kit, or by protein extraction into an organic mix (phenol:chloroform:isoamyl alcohol) and subsequent ethanol precipitation. These methods are limited in scale as they can provide maximally five to ten mg of clean and homogeneous mRNA; thus, they are inadequate for the needs of clinical and commercial uses of mRNA. Recent novel methods, such as tangential flow filtration (TFF) have been modified to purify precipitated mRNA from in vitro transcription reactions; this has greatly increased the scale of purification. Additional methods suitable for the large-scale purification of mRNA, however, can be useful for the continued clinical and commercial development of mRNA therapeutics.

Accordingly, a need exists for a method that produces clean and homogeneous mRNA compositions, e.g., that are usable in purifying an mRNA therapeutic such as an mRNA replacement therapeutic. The method described here is further advantageous in that it addresses this need and in large-scale quantities, yet in a cost-effective manner.

SUMMARY OF THE INVENTION

The present invention relates to methods of purifying messenger RNA, including methods using a stirred cell or agitated Nutsche filtration device for preparing quantities, including large-scale quantities, of clean and homogeneous mRNA compositions, e.g., that are usable in an mRNA replacement therapeutic.

Generally, the methods permit filtration of an mRNA-containing slurry in an enclosed vessel using either pressure or vacuum which separates a mother liquor from the slurry through a filtering screen or membrane.

In embodiments of the method, a high concentration solution of salt (e.g., a chaotropic salt such as guanidine thiocyanate) is added to an initial mRNA-containing composition to denature and solubilize contaminating proteins (e.g., mRNA polymerase and DNase I, which is added after transcription to remove DNA templates) followed by addition of an alcohol (e.g., ethanol) to selectively precipitate mRNA.

After mRNA precipitation, the resulting slurry is continuously stirred within the filtering device while pressure is applied to the slurry to push mother liquid through the filter or vacuum is applied to pull the mother liquor through the filter. Later, the precipitate within the slurry is washed or diafiltered using a salt/alcohol mixture followed by a high percentage alcohol wash to yield a precipitate that is free of contamination, e.g., protein, salt, buffer, and non-mRNA nucleic acid. Subsequent dissolution of the precipitated mRNA by water yields purified mRNA composition. In some embodiments, a solid support, such as polystyrene beads of a known size, are added to increase the purification capacity within a given filtration volume. Accordingly, the present invention is superior to currently-used methods for producing purified mRNA compositions, e.g., for use in mRNA replacement therapeutics. In sum, the present invention represents a significant breakthrough in the mRNA-based therapeutic field.

In one aspect, the present invention features a method of purifying mRNA that includes steps of providing a solution comprising mRNA; adding one or more agents that promote precipitation of mRNA, thereby obtaining a slurry; stirring the slurry prior to and/or while providing pressure to the slurry and/or a vacuum to the slurry sufficient to direct the slurry's mother liquor through a filter, thereby obtaining a precipitate-containing composition; and washing the precipitate-containing composition, thereby yielding a purified mRNA precipitate. In embodiments, a washing is a diafiltering, ultrafiltering, or dialyzing.

In another aspect, the present invention features a method of purifying at least about 1, 2.5, 5, or 10 grams mRNA that includes steps of providing a solution comprising mRNA; adding one or more agents that promote precipitation of mRNA, thereby obtaining a slurry; stirring the slurry prior to and/or while providing pressure to the slurry and/or a vacuum to the slurry sufficient to direct the slurry's mother liquor through a filter, thereby obtaining a precipitate-containing composition; and washing the precipitate-containing composition, thereby yielding a purified mRNA precipitate, and wherein total purified mRNA is recovered in an amount that results in a yield of at least about 80%, 85%, 90%, 91%, 92%, 93%, 94%, or 95%; and/or total purified mRNA is substantially free of prematurely aborted RNA sequences and/or enzyme reagents used in in vitro synthesis. In embodiments, a washing is a diafiltering, ultrafiltering, or dialyzing.

In still another aspect, the present invention features a method of purifying at least about 25, 50, 100, or 1000 grams mRNA that includes steps of providing a solution comprising mRNA; adding one or more agents that promote precipitation of mRNA, thereby obtaining a slurry; stirring the slurry prior to and/or while providing pressure to the slurry and/or a vacuum to the slurry sufficient to direct the slurry's mother liquor through a filter, thereby obtaining a precipitate-containing composition; and washing the precipitate-containing composition, thereby yielding a purified mRNA precipitate, and wherein total purified mRNA is recovered in an amount that results in a yield of at least about 80%, 85%, 90%, 91%, 92%, 93%, 94%, or 95%; and/or total purified mRNA is substantially free of prematurely aborted RNA sequences and/or enzyme reagents used in in vitro synthesis. In embodiments, a washing is a diafiltering, ultrafiltering, or dialyzing.

In embodiments, a stirring step occurs in a stirred cell or a Nutsche Filter.

In embodiments, a step of the adding one or more agents that promote precipitation of mRNA occurs in the stirred cell or in the Nutsche Filter.

In embodiments, a step of adding one or more agents that promote precipitation of mRNA does not occur in the stirred cell or in the Nutsche Filter.

In embodiments, stirring occurs at a speed between about 50 RPM and about 500 RPM. In embodiments, stirring occurs at a speed of about 200 RPM.

In embodiments, the pressure is between about 5 PSI and about 100 PSI.

In embodiments, pressure is about 10 PSI to about 40 PSI.

In embodiments, at least a washing step occurs in a stirred cell or a Nutsche Filter.

In embodiments, a one or more agents that promote precipitation of mRNA comprise an alcohol. In embodiments, an alcohol is ethanol.

In embodiments, a method further comprises comprising adding one or more agents that denatures proteins and/or keeps proteins soluble in an aqueous medium.

In embodiments, a one or more agents that denatures proteins and/or keeps proteins soluble in an aqueous medium comprise a salt.

In embodiments, a salt is a chaotropic salt.

In embodiments, a step of adding one or more agents that denatures proteins and/or keeps proteins soluble in an aqueous medium occurs in the stirred cell or in the Nutsche Filter.

In embodiments, a step of adding one or more agents that denatures proteins and/or keeps proteins soluble in an aqueous medium does not occur in the stirred cell or in the Nutsche Filter.

In embodiments, a method further comprises a step of drying the purified mRNA precipitate. In embodiments, a purified mRNA precipitate is dried by continuing to provide pressure and/or vacuum such that precipitated mRNA is obtained as a cake of precipitate In embodiments, a method further comprises a step of solubilizing the purified mRNA precipitate in an aqueous medium, thereby obtaining a solution comprising purified mRNA.

In embodiments, a step of solubilizing the purified mRNA precipitate comprises adding an aqueous medium. In embodiments, an aqueous medium is water.

In embodiments, a slurry comprises at least one dispersant. In embodiments, a dispersant is one or more of ash, clay, diatomaceous earth, filtering agent, glass beads, plastic beads, polymers, polypropylene beads, polystyrene beads, salts (e.g., cellulose salts), sand, and sugars.

In embodiments, a method further comprises one or more steps for separating the dispersant from the purified mRNA precipitate.

In embodiments, a one or more steps for separating the dispersant from the purified mRNA precipitate comprises washing and drying the cake.

In embodiments, a method further comprises solubilizing and eluting the purified mRNA from the cake using an aqueous medium while filtering the dispersant.

In embodiments, an aqueous medium is water.

In embodiments, a provided solution of mRNA comprises about 500 mg mRNA to about 100 g mRNA, about 100 g mRNA to about 1 kg mRNA, about 500 g mRNA to about 5 kg mRNA, or about 500 g mRNA to about 2.5 kg mRNA.

In embodiments, a one or more agents that promote precipitation of mRNA are a chaotropic salt and an alcohol. In embodiments, a chaotropic salt is guanidine thiocyanate, and an alcohol is ethanol.

In embodiments, mRNA is contacted with the one or more agents that promote precipitation of mRNA for a total amount of about one minute to about one hour, about one minute to about thirty minutes, about one minute to about fifteen minutes, or about one minute to about ten minutes.

In embodiments, a stirring step occurs in a stirred cell, and the pressure is about 20 PSI to about 50 PSI.

In embodiments, each stirring step occurs in a stirred cell.

In embodiments, a washing step comprises contacting the precipitate-containing composition with a first solution comprising a chaotropic salt and an alcohol. In embodiments, a chaotropic salt is guanidine thiocyanate, and an alcohol is ethanol.

In embodiments, a precipitate-containing composition is contacted with said first solution 1-5 times.

In embodiments, a method further comprises a washing step that comprises contacting the precipitate-containing composition with a second solution that is aqueous alcohol.

In embodiments, a second solution is aqueous ethanol.

In embodiments, a precipitate-containing composition is contacted with said second solution 1-10 times.

In embodiments, a washing step occurs in a stirred cell, and the pressure is about 20 PSI to about 50 PSI.

In embodiments, each washing step occurs in a stirred cell.

In embodiments, a method further comprises a step of solubilizing the purified mRNA precipitate in an aqueous medium, thereby obtaining a solution comprising purified mRNA.

In embodiments, a provided solution of mRNA comprises a dispersant.

In embodiments, a dispersant is polymer microspheres.

In embodiments, a stirring step occurs in a Nutsche Filter, and the pressure is about 5 PSI to about 25 PSI.

In embodiments, each stirring step occurs in a Nutsche Filter.

In embodiments, a washing step comprises contacting the precipitate-containing composition with a first solution comprising a chaotropic salt and an alcohol. In embodiments, a chaotropic salt is guanidine thiocyanate, and an alcohol is ethanol.

In embodiments, a precipitate-containing composition is contacted with said first solution 1-5 times.

In embodiments, a method further comprises a washing step that comprises contacting the precipitate-containing composition with a second solution that is aqueous alcohol.

In embodiments, a second solution is aqueous ethanol.

In embodiments, a precipitate-containing composition is contacted with said second solution 1-10 times.

In embodiments, a washing step occurs in a Nutsche Filter, and the pressure is about 5 PSI to about 25 PSI.

In embodiments, each washing step occurs in a Nutsche Filter.

In embodiments, a drying step follows at least one washing step. In embodiments, a drying step follows each washing step. In embodiments, a drying step is a final step of a purification method described herein.

In embodiments, a method further comprises a step of solubilizing the purified mRNA precipitate in an aqueous medium, thereby obtaining a solution comprising purified mRNA.

In another aspect, the invention features a composition comprising dried purified mRNA, wherein said mRNA is obtained by a method described herein.

In embodiments, the invention features a composition comprising dried purified mRNA, wherein said mRNA is obtained by a method comprising: providing a solution comprising mRNA; adding one or more agents that promote precipitation of mRNA, thereby obtaining a slurry; stirring the slurry prior to and/or while providing pressure to the slurry and/or a vacuum to the slurry sufficient to direct the slurry's mother liquor through a filter, thereby obtaining a precipitate-containing composition; and washing the precipitate-containing composition, thereby yielding a purified mRNA precipitate. In embodiments, a washing is a diafiltering, ultrafiltering, or dialyzing.

In embodiments, dried purified mRNA comprises a dispersant. In embodiments, dried purified mRNA is substantially free of any dispersant (e.g., any dispersant used in a method of purification described herein).

In some embodiments, dried purified mRNA is stored at a temperature of about 0° C. to about −40° C. for a period of at least about a week to about two years, a period of up to about two years, or a period of up to about one year.

In some embodiments, dried purified mRNA is reconstituted following storage.

In some embodiments, dried purified mRNA has substantially the same integrity as prior to storage.

In some embodiments, mRNA is in vitro transcribed mRNA.

In some embodiments, mRNA is cap and tail (C/T) mRNA.

In some embodiments, mRNA is final mRNA.

In embodiments, mRNA encodes cystic fibrosis transmembrane conductance regulator protein (CFTR).

In embodiments, mRNA encodes ornithine transcarbamylase (OTC).

Another aspect of the present invention is a composition including a purified mRNA precipitate prepared by the method above.

Yet another aspect of the present invention is a pharmaceutical composition comprising a composition of the present invention and at least one pharmaceutically-acceptable excipient.

Yet another aspect of the present investor is a method for treating a disease or disorder comprising administering to a subject in need thereof a pharmaceutical composition of the present invention.

Any aspect or embodiment described herein can be combined with any other aspect or embodiment as disclosed herein. While the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

Other features and advantages of the invention will be apparent from the Drawings and the following detailed description and claims.

BRIEF DESCRIPTION OF THE DRAWINGS

The above and further features will be more clearly appreciated from the following detailed description when taken in conjunction with the accompanying drawings. The drawings however are for illustration purposes only; not for limitation.

DEFINITIONS

Figure 1:
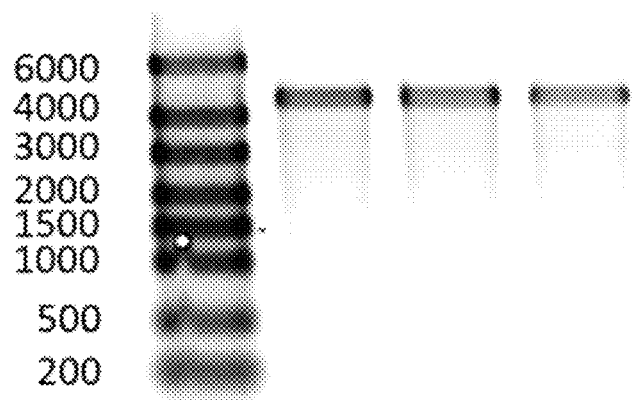
FIG. 1 is a digital image of a 1% Agarose/TAE gel showing: lane 1: mRNA reference ladder; lane 2: CFTR mRNA transcript purified with stirred cell; lane 3: CFTR mRNA transcript purified with Nutsche filter using polystyrene beads; and lane 4: CFTR mRNA transcript purified with Qiagen RNeasy®.

In order for the present invention to be more readily understood, certain terms are first defined below. Additional definitions for the following terms and other terms are set forth throughout the Specification.

As used in this Specification and the appended claims, the singular forms "a," "an" and "the" include plural referents unless the context clearly dictates otherwise.

Unless specifically stated or obvious from context, as used herein, the term "or" is understood to be inclusive and covers both "or" and "and".

The terms "e.g.," and "i.e." as used herein, are used merely by way of example, without limitation intended, and should not be construed as referring only those items explicitly enumerated in the specification.

The terms "or more", "at least", "more than", and the like, e.g., "at least one" are understood to include but not be limited to at least 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more than the stated value. Also included is any greater number or fraction in between.

Conversely, the term "no more than" includes each value less than the stated value. For example, "no more than 100 nucleotides" includes 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, and 0 nucleotides. Also included is any lesser number or fraction in between.

The terms "plurality", "at least two", "two or more", "at least second", and the like, are understood to include but not limited to at least 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more. Also included is any greater number or fraction in between.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

Unless specifically stated or obvious from context, as used herein, the term "about" is understood as within a range of normal tolerance in the art, for example within 2 standard deviations of the mean. "About" can be understood to be within 10%, 9%, 8%, 7%, 6%, 5%, 4%, 3%, 2%, 1%, 0.5%, 0.1%, 0.05%, 0.01%, or 0.001% of the stated value. Unless otherwise clear from the context, all numerical values provided herein are modified by the term "about".

As used herein, the term "batch" refers to a quantity or amount of mRNA synthesized at one time, e.g., produced according to a single manufacturing order during the same cycle of manufacture. A batch may refer to an amount of mRNA synthesized in one reaction that occurs via a single aliquot of enzyme and/or a single aliquot of DNA template for continuous synthesis under one set of conditions. In some embodiments, a batch would include the mRNA produced from a reaction in which not all reagents and/or components are supplemented and/or replenished as the reaction progresses. The term "batch" would not mean mRNA synthesized at different times that are combined to achieve the desired amount.

As used herein, the term "contaminants" refers to substances inside a confined amount of liquid, gas, or solid, which differ from the chemical composition of the target material or compound. Contaminants are also referred to as impurities. Examples of contaminants or impurities include buffers, proteins (e.g., enzymes), nucleic acids, salts, solvents, and/or wash solutions.

As used herein, the term "dispersant" refers to a solid particulate which reduces the likelihood that a mRNA precipitate will form a hydrogel. Examples of dispersants include and are not limited to one or more of ash, clay, diatomaceous earth, filtering agent, glass beads, plastic beads, polymers, polypropylene beads, polystyrene beads, salts (e.g., cellulose salts), sand, and sugars. In embodiments, a dispersant is polymer microspheres (e.g., poly (styrene-co-divinylbenezene) microspheres).

As used herein, "expression" of a nucleic acid sequence refers to one or more of the following events: (1) production of an mRNA template from a DNA sequence (e.g., by transcription); (2) processing of an mRNA transcript (e.g., by splicing, editing, 5' cap formation, and/or 3' end formation); (3) translation of an mRNA into a polypeptide or protein; and/or (4) post-translational modification of a polypeptide or protein. In this application, the terms "expression" and "production," and grammatical equivalent, are used inter-changeably.

As used herein, "full-length mRNA" is as characterized when using a specific assay, e.g., gel electrophoresis or detection using UV and UV absorption spectroscopy with separation by capillary electrophoresis. The length of an mRNA molecule that encodes a full-length polypeptide and as obtained following any of the purification methods described herein is at least 50% of the length of a full-length mRNA molecule that is transcribed from the target DNA, e.g., at least 60%, 70%, 80%, 90%, 91%, 92%, 93%, 94%, 95%, 96%, 97%, 98%, 99%, 99.01%, 99.05%, 99.1%, 99.2%, 99.3%, 99.4%, 99.5%, 99.6%, 99.7%, 99.8%, 99.9% of the length of a full-length mRNA molecule that is transcribed from the target DNA and prior to purification according to any method described herein.

As used herein, a "functional" biological molecule is a biological molecule in a form in which it exhibits a property and/or activity by which it is characterized.

As used herein, the term "hydrogel" refers to a network of hydrophilic polymer chains, e.g., mRNA, which forms a colloidal gel in which water is the dispersion medium. Using mRNA as an example, it is more difficult to extract or purify mRNA from a hydrogel than from a dry cake.

As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man.

As used herein, the term "messenger RNA (mRNA)" refers to a polyribonucleotide that encodes at least one polypeptide. mRNA as used herein encompasses both modified and unmodified mRNA. mRNA may contain one or more coding and non-coding regions. mRNA can be purified from natural sources, produced using recombinant expression systems and optionally purified, in vitro transcribed, or chemically synthesized.

mRNA is typically thought of as the type of RNA that carries information from DNA to the ribosome. The existence of mRNA is usually very brief and includes processing and translation, followed by degradation. Typically, mRNA includes a nucleotide sequence having a coding region that codes for a polypeptide, a 5' untranslated region (5' UTR) upstream of the coding region, a 3'untranslated region (3' UTR) downstream of the coding region, a cap at the 5' terminus and a polyA or polyadenylation region downstream of the 3'UTR. Typically, in eukaryotic organisms, mRNA processing comprises transcription of the mRNA from DNA and the addition of a "cap" on the N-terminal (5') end, and a "tail" on the C-terminal (3') end. A typical cap is a 7-methylguanosine cap, which is a guanosine that is linked through a 5'-5'-triphosphate bond to the first transcribed nucleotide. The presence of the cap is important in providing resistance to nucleases found in most eukaryotic cells. The tail is typically a polyadenylation event whereby a polyadenylyl moiety is added to the 3' end of the mRNA molecule. The presence of this "tail" serves to protect the mRNA from exonuclease degradation. Messenger RNA typically is translated by the ribosomes into a series of amino acids that make up a protein.

In some embodiments, an mRNA of the present invention lacks one or both of a cap and/or a tail. Thus, an mRNA may have a cap and lack a tail, an mRNA may have a tail and lack a cap, and an mRNA may lack a cap and lack a tail.

Any mRNA capable of being translated into one or more peptides (e.g., proteins) or peptide fragments is contemplated as within the scope of the present invention. In some embodiments, an mRNA encodes one or more naturally occurring peptides. In some embodiments, an mRNA encodes one or more modified or non-natural peptides.

As used herein, the term "mRNA integrity" generally refers to the quality of mRNA. In some embodiments, mRNA integrity refers to the percentage of mRNA that is not degraded after a purification process (e.g., a method described herein). mRNA integrity may be determined using methods particularly described herein, such as TAE Agarose gel electrophoresis or by SDS-PAGE with silver staining, or by methods well known in the art, for example, by RNA agarose gel electrophoresis (e.g., Ausubel et al., John Weley & Sons, Inc., 1997, Current Protocols in Molecular Biology).

As used herein, the term "pharmaceutically acceptable", refers to substances that, within the scope of sound medical judgment, are suitable for use in contact with the tissues of human beings and animals without excessive toxicity, irritation, allergic response, or other problem or complication, commensurate with a reasonable benefit/risk ratio.

A "pharmaceutically acceptable excipient" means an excipient that is suitable for preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

Typically, a suitable mRNA solution may also contain a buffering agent and/or salt. Generally, buffering agents can include HEPES, ammonium sulfate, sodium bicarbonate, sodium citrate, sodium acetate, potassium phosphate and sodium phosphate.

Pharmaceutically acceptable salts are well known in the art. For example, S. M. Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. Representative alkali or alkaline earth metal salts include sodium, lithium, potassium, calcium, magnesium, and the like. Further pharmaceutically acceptable salts include, when appropriate, non-toxic ammonium, quaternary ammonium, and amine cations formed using counterions such as halide, hydroxide, carboxylate, sulfate, phosphate, nitrate, sulfonate and aryl sulfonate. Further pharmaceutically acceptable salts include salts formed from the quarternization of an amine using an appropriate electrophile, e.g., an alkyl halide, to form a quarternized alkylated amino salt.

As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena. Unless otherwise defined, all technical and scientific terms used herein have the same meaning as commonly understood by one of ordinary skill in the art to which this application belongs and as commonly used in the art to which this application belongs; such art is incorporated by reference in its entirety. In the case of conflict, the present Specification, including definitions, will control.

DETAILED DESCRIPTION OF THE INVENTION mRNA can present challenges in both synthesis and in purification, particularly in large-scale preparations. The present invention relates to methods using a stirred cell or agitated Nutsche filtration device for preparing quantities of clean and homogeneous mRNA compositions, e.g., that are usable in an mRNA replacement therapeutic.

Thus, methods described herein can be advantageous for the purification of mRNA, including large-scale quantities of mRNA (e.g., any batch size or loading volume described herein). For example, the purification methods as described herein can provide an increased percentage of full-length mRNA that is recovered from the purification relative to the amount of full-length mRNA prior to the purification, e.g., as compared to conventional purification methods. The purification methods as described herein can provide an increased percentage of full-length mRNA relative to the mixture of full-length mRNA and contaminants, e.g., as compared to conventional purification methods. The purification methods as described herein can provide mRNA having a high level of integrity acceptable for therapeutic, with minimal loss of full-length mRNA on account of the purification, e.g., as compared to conventional purification methods. Additionally, purified mRNA (including compositions or batches thereof) prepared according to methods described herein can have beneficial features. For example, a composition or batch of mRNA purified as described herein can: comprise an increased percentage of full-length mRNA molecules; comprise an increased quantity of full-length mRNA; and/or provide an increased activity (e.g., improved or increased protein expression). Such features can be beneficial for therapeutic uses.

Generally, the methods permit filtration of an mRNA-containing slurry in an enclosed vessel using either pressure or vacuum which separates a mother liquor from the slurry through a filtering screen or membrane. Accordingly, the present invention can be superior to currently-used methods for producing purified mRNA compositions on large scale, e.g., scales suitable for use in commercial production of mRNA therapeutics. In sum, the present invention represents a significant breakthrough in the mRNA-based therapeutic field.

Methods of Purification

In one aspect, the present invention provides a method of purifying messenger RNA. In embodiments, a purification method includes steps of: providing a solution comprising mRNA; adding one or more agents that promote precipitation of mRNA, thereby obtaining a slurry ("a precipitating step"); stirring the slurry prior to and/or while providing pressure to the slurry and/or a vacuum to the slurry sufficient to direct the slurry's mother liquor through a filter, thereby obtaining a precipitate-containing composition ("a stirring step"); and washing the precipitate-containing composition, thereby yielding a purified mRNA precipitate ("a washing step"). In embodiments, a washing is a diafiltering, ultrafiltering, or dialyzing.

In some embodiments, a method described herein is used to purify an amount of mRNA that is at least 250 mg mRNA. In one embodiment, a method described herein is used to purify an amount of mRNA that is about 250 mg mRNA, about 500 mg mRNA, about 750 mg mRNA, about 1000 mg mRNA, about 1500 mg mRNA, about 2000 mg mRNA, or about 2500 mg mRNA. In embodiments, a method described herein is used to purify an amount of mRNA that is between 250 mg mRNA and 1,000 g mRNA. In embodiments, a method described herein is used to purify an amount of mRNA that is between 500 mg mRNA and 1,000 g mRNA. In embodiments, a method described herein is used to purify an amount of mRNA that is about 500 mg mRNA to about 1,000 g mRNA, about 500 mg mRNA to about 500 g mRNA, about 500 mg mRNA to about 250 g mRNA, about 500 mg mRNA to about 100 g mRNA, about 500 mg mRNA to about 50 g mRNA, about 500 mg mRNA to about 25 g mRNA, about 500 mg mRNA to about 10 g mRNA, or about 500 mg mRNA to about 5 g mRNA. In embodiments, a method described herein is used to purify an amount of mRNA that is at least about 100 mg mRNA to about 10 g mRNA, about 100 mg mRNA to about 5 g mRNA, or about 100 mg mRNA to about 1 g mRNA.

In some embodiments, a method described herein provides a yield of purified mRNA that is at least about 50%, about 55%, about 60%, about 65%, about 70%, about 75%, about 80%, about 85%, about 90%, or about 95%. In some embodiments, a method described herein provides a yield of purified mRNA that is at least about 70% (e.g., at least about 70%, 75%, 80%, or 85%). In some embodiments, a method described herein provides a yield of purified mRNA that is at least about 85%.

In some embodiments, a method described herein provides purified mRNA that is substantially free of any enzymes or reagents in the solution used prepare the mRNA. In some embodiments, the solution used to prepare the mRNA comprises enzyme reagents used in in vitro synthesis, including RNA polymerases (e.g., T7 RNA polymerase ("T7") and/or SP6 RNA polymerase ("SP6")), DNAse I, pyrophosphatase, and/or RNAse inhibitor, or any combination thereof. In some embodiments, the method described herein provides purified mRNA that is substantially free of T7 RNA polymerase ("T7"). In some embodiments, the method described herein provides purified mRNA that is substantially free of SP6 RNA polymerase ("SP6"). In some embodiments, the method described herein provides purified mRNA that is substantially free of DNAse I. In some embodiments, the method described herein provides purified mRNA that is substantially free of pyrophosphatase. In some embodiments, the method described herein provides purified mRNA that is substantially free of RNAse inhibitor. In some embodiments, the determination of being substantially free of any of the aforementioned enzymes or reagents used prepare the mRNA is conducted by TAE Agarose gel electrophoresis. In some embodiments, the determination of being substantially free of any of the aforementioned enzymes or reagents used prepare the mRNA is conducted by SDS-PAGE with silver staining.

In some embodiments, one or more denaturing agents is used in a denaturing condition to promote precipitation of mRNA. As used herein, the term "denaturing condition" refers to any chemical or physical conditions that can cause denaturation. Exemplary denaturing conditions include, but are not limited to, use of chemical reagents, high temperatures, extreme pH, etc. In some embodiments, a denaturing condition is achieved through adding one or more denaturing agents to an impure preparation containing mRNA to be purified. In some embodiments, a denaturing agent suitable for the present invention is a protein and/or DNA denaturing agent. In some embodiments, a denaturing agent may be: 1) an enzyme (such as a serine proteinase or a DNase), 2) an acid, 3) a solvent, 4) a cross-linking agent, 5) a chaotropic agent, 6) a reducing agent, and/or 7) high ionic strength via high salt concentrations. In some embodiments, a particular agent may fall into more than one of these categories.

In some embodiments, one or more enzymes may be used as denaturing agents to degrade proteins and DNA templates used in mRNA synthesis. In some embodiments, suitable enzymes include, but are not limited to, serine proteases such as chymotrypsin and chymotrypsin-like serine proteases, trypsin and trypsin-like serine proteases, elastase and elastase-like serine proteases, subtilisin and subtilisin-like serine proteases, and combinations thereof, deoxyribonucleases (DNases) such as deoxyribonuclease I, II and/or IV, restriction enzymes such as EcoRI, EcoRII, BamHI, HindIII, SpeI, SphI, StuI, XbaI, and combination thereof.

In some embodiments, an acid may be used as a denaturing agent. In some embodiments, a suitable acid may be acetic acid, formic acid, oxalic acid, citric acid, benzoic acid, chloroacetic acid, dichloroacetic acid, trichloroacetic acid, ascorbic acid, sulfosalicylic acid, and combinations thereof.

In some embodiments, a solvent may be used as a denaturing agent. In some embodiments, a solvent may be isopropyl alcohol, acetone, methyl ethyl ketone, methyl isobutyl ketone, ethanol, methanol, denatonium, and combinations thereof. In embodiments, a solvent is an alcohol solvent (e.g., methanol, ethanol, or isopropanol). In embodiments, a solvent is a ketone solvent (e.g., acetone, methyl ethyl ketone, or methyl isobutyl ketone)

In some embodiments, a chaotropic agent may be used as a denaturing agent. Choatropic agents are substances which disrupt the structure of macromolecules such as proteins and nucleic acids by interfering with non-covalent forces such as hydrogen bonds and van der Waals forces. In some embodiments, a chaotropic agent may be urea, thiourea, guanidinium chloride, guanidinium thiocyanate, guanidinium isothiocyanate, lithium acetate, magnesium chloride, sodium dodecyl sulfate, lithium perchlorate and combination thereof.

In some embodiments, a reducing agent may be used as a denaturing agent. Reducing agents are compounds that donate an electron to another species, thus becoming oxidized itself. In some embodiments, a reducing agent may be lithium aluminum hydride, sodium amalgam, diborane, sodium borohydride, sulfites, diisobutylaluminum hydride, phosphites, carbon monoxide, 2-mercaptoethanol, dithiothreitol, or tris(2-carboxyethyl)phosphine, and combinations thereof.

In some embodiments, one or more of pH, heat, and/or heavy metals (such as lead, mercury or cadmium) may serve as denaturing agents to provide a denaturating condition. Extremes of pH are known to cause a protein to denature. Although the backbone of a protein chain is neutral, the amino acid residues that comprise the protein often contain acidic and basic groups. These groups are usually charged and can form salt bridges with a group of opposite charge. Accordingly, extremes of pH can change the charges on these acidic and basic groups, disrupting salt bridges.

In some embodiments, less drastic changes in pH may also affect the activity and solubility of a protein. Like individual amino acids, proteins have an isoelectric point at which the number of negative charges equals the number of positive charges. This is frequently the point of minimum water solubility. At the isoelectric pH, there is no net charge on the molecule. Individual molecules have a tendency to approach one another, coagulate, and precipitate out of solution. At a pH above or below the isoelectric pH, the molecules have a net negative or positive charge, respectively. Thus when protein molecules approach each other, they have the same overall charge and repulse each other.

In some embodiments, heat may be used as a denaturing agent. Heat can supply kinetic energy to protein molecules, causing their atoms to vibrate more rapidly. In some embodiments, this will disrupt relatively weak forces such as hydrogen bonds and hydrophobic interactions. Heat is also used in sterilization to denature and hence destroy the enzymes in bacteria.

In some embodiments, salts of metal ions such as mercury (II), lead(II), and silver may be used as denaturing agents due to their ability to form strong bonds with disulfide groups and with the carboxylate ions of the acidic amino acids. Thus, they disrupt both disulfide bridges and salt linkages and cause the protein to precipitate out of solution as an insoluble metal-protein salt.

In some embodiments, high concentrations of salt (high salinity) may also be used as a denaturing agent. High concentrations of salts are known to cause both proteins and nucleic acids to precipitate from an aqueous solution. In some embodiments, a high concentration of salt may be between 1M and 10M, inclusive. In some embodiments, a high concentration of salt may be between 2M and 9M, inclusive. In some embodiments, a high concentration of salt may be between 2M and 8M, inclusive. In some embodiments, a high concentration of salt may be between 2M and 5M, inclusive. In some embodiments, a high concentration of salt may be greater than 1M concentration. In some embodiments, a high concentration of salt may be greater than 2M concentration. In some embodiments, a high concentration of salt may be greater than 3M concentration. In some embodiments, a high concentration of salt may be greater than 4M concentration. In some embodiments, a high concentration of salt may be greater than 5M concentration. In some embodiments, a high concentration of salt may be greater than 6M concentration. In some embodiments, a high concentration of salt may be greater than 7M concentration. In some embodiments, a high concentration of salt may be greater than 8M concentration. In some embodiments, a single salt is used as a denaturing agent. In some embodiments, more than one salt is used as a denaturing agent.

In some embodiments, a salt used as a denaturing agent may be a calcium salt, an iron salt, a magnesium salt, a potassium salt, a sodium salt, or a combination thereof. Exemplary specific salts suitable for use as denaturing agents in some embodiments include, but are not limited to, potassium chloride (KCl), sodium chloride (NaCl), lithium chloride (LiCl), calcium chloride ($CaCl_2$), potassium bromide (KBr), sodium bromide (NaBr), lithium bromide (LiBr). In some embodiments, the denaturing agent the impure preparation is subjected to is potassium chloride (KCl). In some embodiments, KCl is added such that the resulting KCl concentration is about 1M or greater. In some embodiments, KCl is added such that the resulting KCl concentration is about 2 M or greater, 3 M or greater, 4 M or greater, or 5 M or greater.

In one embodiment, a high concentration solution of salt (e.g., a chaotropic salt such as guanidine thiocyanate) is added to an initial mRNA-containing composition to denature and solubilize contaminating proteins followed by addition of an alcohol (e.g., ethanol) to selectively precipitate mRNA. After mRNA precipitation, the resulting slurry is continuously stirred within the filtering device while pressure is applied to the slurry to push mother liquid through the filter or vacuum is applied to pull the mother liquor through the filter. Later, the precipitate within the slurry is washed or diafiltered using a salt/alcohol mixture followed by a high percentage alcohol wash to yield a precipitate that is free of contamination, e.g., protein, salt, buffer, and non-RNA nucleic acid. Subsequent dissolution of the precipitated mRNA by water yields purified mRNA composition. In some embodiments, a solid support, such as polystyrene beads of a known size, are added to increase the purification capacity within a given filtration volume.

In embodiments of the methods, a precipitating step comprises the use of a chaotropic salt (e.g., guanidine thiocyanate) and/or an alcohol solvent (e.g., an aqueous solution of alcohol such as an aqueous ethanol solution). In embodiments of the methods, a precipitating step comprises the use of a chaotropic salt (e.g., guanidine thiocyanate) and an alcohol solvent (e.g., an aqueous solution of alcohol such as an aqueous ethanol solution).

In embodiments, one or more agents that promote precipitation of mRNA comprises guanidine thiocyanate (e.g., a solution comprising about 1-5M guanidine thiocyanate). In embodiments, an agent that promotes precipitation of mRNA is a GSCN buffer (e.g., an aqueous solution comprising 4M guanidine thiocyanate, 25 mM sodium citrate pH 6.5, 0.5% N-lauroylsarcosine sodium salt).

In embodiments, one or more agents that promote precipitation of mRNA includes an alcohol solvent (e.g., ethanol). In embodiments, one or more agents that promote precipitation of mRNA is an aqueous solution of an alcohol (e.g., aqueous ethanol).

In embodiments, two agents are used to promote precipitation of mRNA, wherein one agent comprises guanidine thiocyanate (e.g., an aqueous solution of guanidine thiocyanate such as a GSCN buffer) and a second agent comprises an alcohol solvent (e.g., ethanol). In embodiments, the two agents are used sequentially or simultaneously. In embodiments, the method includes use of a solution comprising guanidine thiocyanate (e.g., a GSCN buffer) and an alcohol (e.g., an aqueous solution of an alcohol such as aqueous ethanol).

In embodiments, a step of the adding one or more agents that promote precipitation of mRNA is performed once. In embodiments, a step of adding one or more agents that promote precipitation of mRNA is performed two or more times (e.g., 2-10 times or 2-5 times). In embodiments, the step of adding one or more agents that promote precipitation of mRNA is performed two, three, four, five, six, seven, eight, nine, or ten times.

In some embodiments, a filtration aid is used in a method described herein. In embodiments, a filtration aid is a dispersant.

In some embodiments, a step of adding one or more agents that promotes precipitation of mRNA is performed in the absence of any dispersants. In embodiments of the method wherein at least one step occurs in a stirred cell, a step of adding one or more agents that promotes precipitation of mRNA is performed in the absence of any dispersants.

In some embodiments, a step of adding one or more agents that promotes precipitation of mRNA is performed in the presence of at least one dispersant. In embodiments of the method wherein at least one step occurs in a Nutsche Filter, a step of adding one or more agents that promotes precipitation of mRNA is performed in the presence of at least one dispersant.

In some embodiments, a dispersant is added to the slurry obtained following the addition of one or more agents that promotes precipitation of mRNA.

Examples of dispersants include and are not limited to one or more of ash, clay, diatomaceous earth, filtering agent, glass beads, plastic beads, polymers, polypropylene beads, polystyrene beads, salts (e.g., cellulose salts), sand, and sugars.

The method may further include a step of drying the purified mRNA precipitate which is included in a cake along with the dispersant. The development of purification methods in which a purified mRNA can be dried to a cake can be challenging due to considerations of, e.g., fouling of a filter. Nonetheless, purification methods comprising drying mRNA to a solid cake can be advantageous as such methods permit removal of residual contaminants in solution to levels that would not be achieved with solution filtration absent large volume exchanges. In embodiments, drying of a purified mRNA is via maintaining pressures described herein such that substantially all liquid is removed from an mRNA composition and thereby results in a cake of comprising purified mRNA precipitate and a dispersant.

Thus, in embodiments, a purification method may further include one or more steps for separating the dispersant from the purified mRNA precipitate, e.g., washing and drying the cake. The method may further include a step of solubilizing and eluting the purified mRNA from the cake using an aqueous medium, e.g., water, while filtering the dispersant. In embodiments, a precipitating step and a drying step may be performed simultaneously.

In embodiments, a drying step has a duration such that the obtained cake is substantially dry. In embodiments, a drying step has a duration of about five seconds to about fifteen minutes, about five seconds to about ten minutes, of about one minute to about fifteen minutes, of about one minute to about ten minutes, of about one minute to about seven minutes, or of about one minute to about five minutes.

In some embodiments, a step of adding one or more agents that promote precipitation of mRNA has a duration of about 5 seconds to about 5 minutes. In some embodiments, a step of adding one or more agents that promote precipitation has a duration of about 30 seconds to about 180 seconds (e.g., about 30 seconds to about 150 seconds). In some embodiments, a step of adding one or more agents that promote precipitation has a duration of about 30, 40, 50, 60, 70, 80, 90, 100, 110, 120, 130, 140, or 150 seconds.

In some embodiments, a step of adding one or more agents that promote precipitation of mRNA has a duration of about one to about ten minutes. In some embodiments, a step of adding one or more agents that promote precipitation of mRNA has a duration of about 120 seconds to about 500 seconds or about 120 seconds to about 240 seconds.

In some embodiments, mRNA is stirred with the one or more agents that promote precipitation of mRNA for a total duration of about one minute to about one hour, about one minute to about thirty minutes, about one minute to about fifteen minutes, or about one minute to about ten minutes. In embodiments, mRNA is stirred with a chaotropic agent (e.g., guanidine thiocyanate) and/or an alcohol (e.g., ethanol).

In some embodiments, a step of the adding one or more agents that promote precipitation of mRNA occurs in a stirred cell or in a Nutsche Filter.

In some embodiments, a step of the adding one or more agents that promote precipitation of mRNA occurs in a stirred cell. In embodiments, the pressure is between about 5 PSI and about 100 PSI, e.g., about 10 PSI to about 40 PSI or about 10 PSI to about 50 PSI.

In some embodiments, a step of the adding one or more agents that promote precipitation of mRNA occurs in a Nutsche Filter, and the pressure is between about 5 PSI and about 100 PSI, e.g., about 10 PSI to about 40 PSI, about 5 PSI to about 30 PSI, or about 5 PSI to about 25 PSI. In embodiments, a dispersant is present during the precipitating step.

In embodiments, a step of the adding one or more agents that promote precipitation of mRNA does not occur in the stirred cell or in the Nutsche Filter.

In some embodiments, at least a stirring step occurs in a stirred cell or a Nutsche Filter. In some embodiments, at least a stirring step occurs in a stirred cell. In some embodiments, at least a stirring step occurs in a Nutsche Filter.

In some embodiments, stirring occurs at a speed of about 50 RPM and about 500 RPM, e.g., about 200 RPM. In embodiments, stirring occurs at a speed of about 100 RPM to about 500 RPM, about 100 RPM to about 400 RPM, about 100 RPM to about 300 RPM, or about 150 RPM to about 450 RPM. In embodiments, stirring occurs at a speed of about: 50, 75, 100, 125, 150, 175, 200, 225, 250, 275, 300, 325, 350, 375, 400, 425, 450, 475, or 500 RPM.

In some embodiments, the pressure is between about 5 PSI and about 100 PSI, e.g., about 10 PSI to about 40 PSI or about 10 PSI to about 50 PSI. In some embodiments, the pressure is between about 10 PSI to about 90 PSI, about 10 PSI to about 80 PSI, about 10 PST to about 70 PSI, about 10 PSI to about 60 PSI, about 10 PSI to about 50 PSI, about 10 PSI to about 40 PSI, about 10 PSI to about 30 PSI, about 10 PSI to about 20 PSI, about 5 PSI to about 30 PSI, about 5 PSI to about 25 PSI, or about 5 PSI to about 20 PSI. In embodiments, the pressure is about 5 PSI, about 10 PSI, about 15 PSI, about 20 PSI, about 25 PSI, about 30 PSI, about 35 PSI, about 40 PSI, about 45 PSI, or about 50 PSI.

In embodiments, at least a stirring step occurs in a stirred cell, and the pressure is between about 5 PSI and about 100 PSI, e.g., about 10 PSI to about 40 PSI or about 10 PSI to about 50 PSI.

In embodiments, at least a stirring step occurs in a Nutsche Filter, and the pressure is between about 5 PSI and about 100 PSI, e.g., about 10 PSI to about 40 PSI, about 5 PSI to about 30 PSI, or about 5 PSI to about 25 PSI.

In embodiments, a stirring step comprises stirring with at least one solution comprising a denaturing agent. In embodiments, a stirring step comprises stirring with at least one solution comprising guanidine thiocyanate (e.g., a GSCN buffer) and/or at least one solution comprising an alcohol solvent (e.g., ethanol). In embodiments, a stirring step comprises stirring with a solution comprising guanidine thiocyanate (e.g., a GSCN buffer) and an alcohol solvent (e.g., ethanol).

In embodiments, a stirring step is performed 1-20, 1-15, 1-10, or 1-5 times. In embodiments, a stirring step is performed once. In embodiments, a stirring step is performed two or more times (e.g., 2-20 times, 2-15 times, 2-10 times or 2-5 times). In embodiments, a stirring step is performed 1-10 or 1-5 times. In embodiments, a stirring step is performed one, two, three, four, five, six, seven, eight, nine, or ten times.

In some embodiments, a stirring step has a duration of about 5 seconds to about 5 minutes. In some embodiments, a stirring step has a duration of about 60 seconds to about 180 seconds (e.g., about 60 seconds to about 150 seconds or about 60 seconds to about 120 seconds). In some embodiments, a stirring step has a duration of about 60, 70, 80, 90, 100, 110, 120, 130, 140, or 150 seconds.

In some embodiments, a stirring step has a duration of about one to about ten minutes. In some embodiments a stirring step has a duration of about 120 seconds to about 500 seconds or about 240 seconds to about 300 seconds.

In some embodiments, a washing step comprises washing a precipitate-containing composition with a solution comprising an alcohol (e.g., an aqueous solution comprising an alcohol. In embodiments, a solution is an aqueous solution that is about 10, 20, 30, 40, 50, 60, 70, 80, or 90% alcohol (e.g., ethanol). In embodiments, an aqueous solution is an about 80% ethanol solution. In embodiments, a washing is a diafiltering, ultrafiltering, or dialyzing.

In some embodiments, at least a washing step occurs in a stirred cell or a Nutsche Filter.

In some embodiments, at least a washing step occurs in a stirred cell, and the pressure is between about 5 PSI and about 100 PSI, e.g., about 10 PSI to about 40 PSI or about 10 PSI to about 50 PSI.

In embodiments, at least a washing step occurs in a Nutsche Filter, and the pressure is between about 5 PSI and about 100 PSI, e.g., about 10 PSI to about 40 PSI, about 5 PSI to about 30 PSI, or about 5 PSI to about 25 PSI.

In embodiments, a washing step is performed 1-20, 1-15, 1-10, or 1-5 times. In embodiments, a washing step is performed once. In embodiments, a washing step is performed two or more times (e.g., 2-20 times, 2-15 times, 2-10 times or 2-5 times). In embodiments, a washing step is performed 1-10 or 1-5 times. In embodiments, a stirring step is performed one, two, three, four, five, six, seven, eight, nine, or ten times.

In some embodiments, a washing step has a duration of about 5 seconds to about 5 minutes. In some embodiments, a washing step has a duration of about 30 seconds to about 120 seconds (e.g., about 30 seconds to about 80 seconds). In some embodiments, a washing step has a duration of about 30, 40, 50, 60, 70, 80, 90, 100, 110, or 120 seconds.

In some embodiments, a washing step has a duration of about one to about ten minutes. In some embodiments a washing step has a duration of about 120 seconds to about 500 seconds, or about 150 seconds to about 450 seconds.

In embodiments, a method comprises 1-5 precipitating steps; 1-5 stirring steps, and 1-10 washing steps. In embodiments, each step has a duration of about 15 seconds to about 180 seconds. In embodiments, a method comprises at least one drying step (e.g., 1-20, 1-15, 1-10, or 1-5 drying steps). In embodiments, a drying step follows a washing step of any method described herein. In embodiments, a drying step is a final step of a method described herein. A final drying step results in a dried cake comprising purified mRNA and optionally a dispersant when used in a method as described herein. A dried cake comprising purified mRNA can have unexpectedly increased stability (e.g., as compared to mRNA purified according to other methods).

In embodiments, at least one step of a method is performed in a stirred cell. In embodiments, at least one precipitating step, at least one stirring step, and at least one washing step are performed in a stirred cell. In embodiments, each step of a method (e.g., each precipitating step, each stirring step, and each washing step) is performed in a stirred cell.

In embodiments, at least one step of a method is performed in a Nutsche Filter. In embodiments, at least one precipitating step, at least one stirring step, and at least one washing step are performed in a Nutsche Filter. In embodiments, each step of a method (e.g., each precipitating step, each stirring step, and each washing step) is performed in a Nutsche Filter.

Characterization of Purified mRNA

In various embodiments, the present invention may be used to purify mRNA in vitro synthesized from an impure preparation containing an in vitro mRNA synthesis reaction mixture. In some embodiments, the impure preparation comprises prematurely aborted RNA sequences and/or enzyme reagents used in in vitro synthesis.

In some embodiments, the purified mRNA molecules are detected using blotting, capillary electrophoresis, chromatography, fluorescence, gel electrophoresis, HPLC, silver stain, spectroscopy, ultraviolet (UV), or UPLC, or a combination thereof. Other detection methods known in the art are included in the present invention.

In various embodiments, mRNA purified according a method described herein is substantially free of impurities from mRNA synthesis process including, but not limited to, prematurely aborted mRNA sequences, DNA templates, and/or enzyme reagents used in in vitro synthesis.

In some embodiments, a method described herein can remove a high degree of enzyme reagents used in in vitro synthesis including, but not limited to, RNA polymerases (e.g., T7 RNA polymerase or SP6 RNA polymerase), DNAse I, pyrophosphatase, and/or RNAse inhibitor. In some embodiments, the present invention is particularly effective to remove T7 RNA polymerase. In some embodiments, the present invention is particularly effective to remove SP6 RNA polymerase. In some embodiments, a method according to the invention removes more than about 90%, 95%, 96%, 97%, 98%, 99% or substantially all enzyme reagents used in in vitro synthesis. In some embodiments, mRNA purified according to the present invention is substantially free of enzyme reagents used in in vitro synthesis. In some embodiments, mRNA purified according to the present invention contains less than about 5% (e.g., less than about 4%, 3%, 2%, or 1%) of enzyme reagents used in in vitro synthesis. In some embodiments, mRNA purified according to the present invention contains less than about 1% (e.g., less than about 0.9%, 0.8%, 0.7%, 0.6%, 0.5%, 0.4%, 0.3%, 0.2%, or 0.1%) of enzyme reagents used in in vitro synthesis. In some embodiments, mRNA purified according to the present invention contains undetectable enzyme reagents used in in vitro synthesis including as determined by, e.g., agarose gel electrophoresis with ethidium bromide and/or Coomassie staining. The percentages of enzyme reagents as described above can be determined by densitometry quantification of agarose gel electrophoresis. Alternatively, the percentages of enzyme reagents as described above can be determined by known techniques, such as by known chromatographic separation and quantification methods.

In some embodiments, the purified mRNA molecules are detected using UV absorption spectroscopy with separation by capillary electrophoresis. In this embodiment, a composition or a batch provides a lower number of peaks, peaks with a narrower base, and/or taller peaks when detected using capillary electrophoresis relative to a composition or a batch having a lower percentage of full-length mRNA molecules. For example, the composition or the batch provides a lower number of peaks, peaks with a narrower base, and/or taller peaks when detected using capillary electrophoresis relative to a composition or a batch including mRNA transcribed using T7 or SP6 as described herein.

In some embodiments, a method according to the invention removes more than about 90% of T7 RNA polymerase used in in vitro synthesis. In some embodiments, a method according to the invention removes more than about 95% of T7 RNA polymerase used in in vitro synthesis. In some embodiments, a method according to the invention removes more than about 98% of T7 RNA polymerase used in in vitro synthesis. In some embodiments, a method according to the invention removes more than about 99% of T7 RNA polymerase used in in vitro synthesis. In some embodiments, a method according to the invention removes substantially all T7 RNA polymerase used in in vitro synthesis. In some embodiments, mRNA purified according to the present invention contains less than about 5% (e.g., less than about 4%, 3%, 2%, or 1%) of T7 polymerase used in in vitro synthesis. In some embodiments, mRNA purified according to the present invention contains less than about 1% (e.g., less than about 0.9%, 0.8%, 0.7%, 0.6%, 0.5%, 0.4%, 0.3%, 0.2%, or 0.1%) of T7 polymerase used in in vitro synthesis. In some embodiments, mRNA purified according to the present invention contains undetectable T7 polymerase used in in vitro synthesis including as determined by, e.g., agarose gel electrophoresis with ethidium bromide and/or Coomassie staining. The percentages of T7 polymerase as described above can be determined by densitometry quantification of agarose gel electrophoresis. Alternatively, the percentages of T7 polymerase as described above can be determined by known techniques, such as by known chromatographic separation and quantification methods.

In some embodiments, a method according to the invention removes more than about 90% of SP6 RNA polymerase used in in vitro synthesis. In some embodiments, a method according to the invention removes more than about 95% of SP6 RNA polymerase used in in vitro synthesis. In some embodiments, a method according to the invention removes more than about 98% of SP6 RNA polymerase used in in vitro synthesis. In some embodiments, a method according to the invention removes more than about 99% of SP6 RNA polymerase used in in vitro synthesis. In some embodiments, a method according to the invention removes substantially all SP6 RNA polymerase used in in vitro synthesis. In some embodiments, mRNA purified according to the present invention contains less than about 5% (e.g., less than about 4%, 3%, 2%, or 1%) of SP6 polymerase used in in vitro synthesis. In some embodiments, mRNA purified according to the present invention contains less than about 1% (e.g., less than about 0.9%, 0.8%, 0.7%, 0.6%, 0.5%, 0.4%, 0.3%, 0.2%, or 0.1%) of SP6 polymerase used in in vitro synthesis. In some embodiments, mRNA purified according to the present invention contains undetectable SP6 polymerase used in in vitro synthesis including as determined by, e.g., agarose gel electrophoresis with ethidium bromide and/or Coomassie staining. The percentages of SP6 polymerase as described above can be determined by densitometry quantification of agarose gel electrophoresis. Alternatively, the percentages of SP6 polymerase as described above can be determined by known techniques, such as by known chromatographic separation and quantification methods.

In some embodiments, a method according to the invention removes more than about 90% of DNAse I used in in vitro synthesis. In some embodiments, a method according to the invention removes more than about 95% of DNAse I used in in vitro synthesis. In some embodiments, a method according to the invention removes more than about 98% of DNAse I used in in vitro synthesis. In some embodiments, a method according to the invention removes more than about 99% of DNAse I used in in vitro synthesis. In some embodiments, a method according to the invention removes substantially all DNAse I used in in vitro synthesis. In some embodiments, mRNA purified according to the present invention contains less than about 5% (e.g., less than about 4%, 3%, 2%, or 1%) of DNAse I used in in vitro synthesis. In some embodiments, mRNA purified according to the present invention contains less than about 1% (e.g., less than about 0.9%, 0.8%, 0.7%, 0.6%, 0.5%, 0.4%, 0.3%, 0.2%, or 0.1%) of DNAse I used in in vitro synthesis. In some embodiments, mRNA purified according to the present invention contains undetectable DNAse I used in in vitro synthesis including as determined by, e.g., agarose gel electrophoresis with ethidium bromide and/or Coomassie staining. The percentages of DNAse I as described above can be determined by densitometry quantification of agarose gel electrophoresis. Alternatively, the percentages of DNAse I as described above can be determined by known techniques, such as by known chromatographic separation and quantification methods.

In some embodiments, a method according to the invention removes more than about 90% of pyrophosphatase used in in vitro synthesis. In some embodiments, a method according to the invention removes more than about 95% of pyrophosphatase used in in vitro synthesis. In some embodiments, a method according to the invention removes more than about 98% of pyrophosphatase used in in vitro synthesis. In some embodiments, a method according to the invention removes more than about 99% of pyrophosphatase used in in vitro synthesis. In some embodiments, a method according to the invention removes substantially all pyrophosphatase used in in vitro synthesis. In some embodiments, a method according to the invention removes substantially all pyrophosphatase used in in vitro synthesis. In some embodiments, mRNA purified according to the present invention contains less than about 5% (e.g., less than about 4%, 3%, 2%, or 1%) of pyrophosphatase used in in vitro synthesis. In some embodiments, mRNA purified according to the present invention contains less than about 1% (e.g., less than about 0.9%, 0.8%, 0.7%, 0.6%, 0.5%, 0.4%, 0.3%, 0.2%, or 0.1%) of pyrophosphatase used in in vitro synthesis. In some embodiments, mRNA purified according to the present invention contains undetectable pyrophosphatase used in in vitro synthesis including as determined by, e.g., agarose gel electrophoresis with ethidium bromide and/or Coomassie staining. The percentages of pyrophosphatase as described above can be determined by densitometry quantification of agarose gel electrophoresis. Alternatively, the percentages of pyrophosphatase as described above can be determined by known techniques, such as by known chromatographic separation and quantification methods.

In some embodiments, a method according to the invention removes more than about 90% of RNAse inhibitor used in in vitro synthesis. In some embodiments, a method according to the invention removes more than about 95% of RNAse inhibitor used in in vitro synthesis. In some embodiments, a method according to the invention removes more than about 98% of RNAse inhibitor used in in vitro synthesis. In some embodiments, a method according to the invention removes more than about 99% of RNAse inhibitor used in in vitro synthesis. In some embodiments, a method according to the invention removes substantially all RNAse inhibitor used in in vitro synthesis. In some embodiments, mRNA purified according to the present invention contains less than about 5% (e.g., less than about 4%, 3%, 2%, or 1%) of RNAse inhibitor used in in vitro synthesis. In some embodiments, mRNA purified according to the present invention contains less than about 1% (e.g., less than about 0.9%, 0.8%, 0.7%, 0.6%, 0.5%, 0.4%, 0.3%, 0.2%, or 0.1%) of RNAse inhibitor used in in vitro synthesis. In some embodiments, mRNA purified according to the present invention contains undetectable RNAse inhibitor used in in vitro synthesis including as determined by, e.g., agarose gel electrophoresis with ethidium bromide and/or Coomassie staining. The percentages of RNAse inhibitor as described above can be determined by densitometry quantification of agarose gel electrophoresis. Alternatively, the percentages of RNAse inhibitor as described above can be determined by known techniques, such as by known chromatographic separation and quantification methods.

For example, a method described herein can remove or eliminate a high degree of prematurely aborted mRNA sequences (also known as "shortmers"). In some embodiments, a method according to the invention removes more than about 90%, 95%, 96%, 97%, 98%, 99% or substantially all prematurely aborted mRNA sequences. In some embodiments, mRNA purified according to the present invention is substantially free of prematurely aborted mRNA sequences. In some embodiments, mRNA purified according to the present invention contains less than about 5% (e.g., less than about 4%, 3%, 2%, or 1%) of prematurely aborted mRNA sequences. In some embodiments, mRNA purified according to the present invention contains less than about 1% (e.g., less than about 0.9%, 0.8%, 0.7%, 0.6%, 0.5%, 0.4%, 0.3%, 0.2%, or 0.1%) of prematurely aborted mRNA sequences. In some embodiments, mRNA purified according to the present invention contains undetectable prematurely aborted mRNA sequences as determined by, e.g., agarose gel electrophoresis with eithidium bromide and/or Coomassie staining. In some embodiments, prematurely aborted mRNA sequences comprise less than 15 bases (e.g., less than 14, 13, 12, 11, 10, 9 or 8 bases). In some embodiments, the prematurely aborted mRNA sequences comprise about 8-12 bases. In some embodiments, a method described herein provides a composition having an increased quantity, e.g., at least two-fold, three-fold, four-fold, five-fold, or more, of full-length polypeptides relative to a composition having a lower percentage of full-length mRNA molecules.

In some embodiments, a purified mRNA solution contains less than about 5% (e.g., less than about 4.5%, 4%, 3.5%, 3%, 2.5%, 2%, 1.5%, 1%, 0.5%, 0.1%) of prematurely aborted RNA sequences and/or enzyme reagents used in in vitro synthesis. In certain embodiments, the purified mRNA solution contains less than about 1% (e.g., less than about 0.9%, 0.8%, 0.7%, 0.6%, or 0.5%) of prematurely aborted RNA sequences and/or enzyme reagents used in in vitro synthesis. In certain embodiments, a purified mRNA solution contains less than about 0.5% (e.g., less than about 0.4%, 0.3%, 0.2%, or 0.1%) of prematurely aborted RNA sequences and/or enzyme reagents used in in vitro synthesis. In some embodiments, a purified mRNA solution contains less than about 0.1% of prematurely aborted RNA sequences and/or enzyme reagents used in in vitro synthesis. In some embodiments, a purified mRNA solution is substantially free of prematurely aborted RNA sequences and/or enzyme reagents used in in vitro synthesis.

In some embodiments, prematurely aborted RNA sequences and/or enzyme reagents used in in vitro synthesis are measured via silver stain, gel electrophoresis, high-performance liquid chromatography (HPLC), ultra-performance liquid chromatography (UPLC), and/or capillary electrophoresis.

In some embodiments, the prematurely aborted RNA sequences contain less than 15 bases (e.g., less than 14, 13, 12, 11, 10, 9, 8, 7, 6, 5, 4, or 3 bases). In some embodiments, the prematurely aborted RNA sequences contain about 8-15, 8-14, 8-13, 8-12, 8-11, or 8-10 bases.

In some embodiments, mRNA purified using a method described herein maintain high degree of integrity. mRNA integrity may be determined using methods particularly described herein, such as TAE Agarose gel electrophoresis or by SDS-PAGE with silver staining, or by methods well known in the art, for example, by RNA agarose gel electrophoresis. In some embodiments, mRNA purified according to the present invention has an integrity greater than about 95% (e.g., greater than about 96%, 97%, 98%, 99% or more). In some embodiments, mRNA purified according to the present invention has an integrity greater than 98%. In some embodiments, mRNA purified according to the present invention has an integrity greater than 99%. In some embodiments, mRNA purified according to the present invention has an integrity of approximately 100%. In some embodiments, a method described herein provides a composition having an increased activity, e.g., at least two-fold, three-fold, four-fold, five-fold, or more, of translated polypeptides relative to a composition having a lower percentage of full-length mRNA molecules.

A particular advantage provided by the present invention is the ability to purify mRNA, in particular, mRNA synthesized in vitro, at a large or commercial scale. For example, in vitro synthesized mRNA may be purified at a scale of or greater than about 1 gram, 10 gram, 50 gram, 100 gram, 200 gram, 300 gram, 400 gram, 500 gram, 600 gram, 700 gram, 800 gram, 900 gram, 1 kg, 5 kg, 10 kg, 50 kg, 100 kg, 1000 kg, or 10000 kg per batch. In embodiments, in vitro synthesized mRNA may be purified at a scale of or greater than about 1 kg.

In one particular embodiment, in vitro synthesized mRNA may be purified at a scale of 10 gram per batch. In one particular embodiment, in vitro synthesized mRNA may be purified at a scale of 20 gram per batch. In one particular embodiment, in vitro synthesized mRNA may be purified at a scale of 25 gram per batch. In one particular embodiment, in vitro synthesized mRNA may be purified at a scale of 50 gram per batch. In another particular embodiment, in vitro synthesized mRNA may be purified at a scale of 100 gram per batch. In yet another particular embodiment, in vitro synthesized mRNA may be purified at a scale of 1 kg per batch. In yet another particular embodiment, in vitro synthesized mRNA may be purified at a scale of 10 kg per batch. In yet another particular embodiment, in vitro synthesized mRNA may be purified at a scale of 100 kg per batch. In yet another particular embodiment, in vitro synthesized mRNA may be purified at a scale of 1,000 kg per batch. In yet another particular embodiment, in vitro synthesized mRNA may be purified at a scale of 10,000 kg per batch.

As shown in the examples below, a batch comprising purified mRNA in the amount of 10 grams or greater (e.g., 25 grams, 50 grams, or 100 grams, or more) can be achieved easily with the methods of the invention.

In some embodiments, the mRNA is purified at a scale of or greater than 1 gram, 5 gram, 10 gram, 15 gram, 20 gram, 25 gram, 30 gram, 35 gram, 40 gram, 45 gram, 50 gram, 75 gram, 100 gram, 150 gram, 200 gram, 250 gram, 300 gram, 350 gram, 400 gram, 450 gram, 500 gram, 550 gram, 600 gram, 650 gram, 700 gram, 750 gram, 800 gram, 850 gram, 900 gram, 950 gram, 1 kg, 2.5 kg, 5 kg, 7.5 kg, 10 kg, 25 kg, 50 kg, 75 kg, or 100 kg per batch.

In some embodiments, the solution comprising mRNA includes at least one gram, ten grams, one-hundred grams, one kilogram, ten kilograms, one-hundred kilograms, one metric ton, ten metric tons, or more mRNA, or any amount there between. In some embodiments, a method described herein is used to purify an amount of mRNA that is at least about 250 mg mRNA. In one embodiment, a method described herein is used to purify an amount of mRNA that is at least about 250 mg mRNA, about 500 mg mRNA, about 750 mg mRNA, about 1000 mg mRNA, about 1500 mg mRNA, about 2000 mg mRNA, or about 2500 mg mRNA. In embodiments, a method described herein is used to purify an amount of mRNA that is at least about 250 mg mRNA to about 500 g mRNA. In embodiments, a method described herein is used to purify an amount of mRNA that is at least about 500 mg mRNA to about 250 g mRNA, about 500 mg mRNA to about 100 g mRNA, about 500 mg mRNA to about 50 g mRNA, about 500 mg mRNA to about 25 g mRNA, about 500 mg mRNA to about 10 g mRNA, or about 500 mg mRNA to about 5 g mRNA. In embodiments, a method described herein is used to purify an amount of mRNA that is at least about 100 mg mRNA to about 10 g mRNA, about 100 mg mRNA to about 5 g mRNA, or about 100 mg mRNA to about 1 g mRNA.

In some embodiments, a method described herein provides a recovered amount of purified mRNA that is at least about 50%, about 55%, about 60%, about 65%, about 70%, about 75%, about 80%, about 85%, about 90%, or about 95%. In some embodiments, a method described herein provides a recovered amount of purified mRNA that is at least about 70% (e.g., at least about 70%, 75%, 80%, or 85%).

Thus, in some embodiments, a method for purifying mRNA using a Nutsche Filter or a stirred cell, wherein the method comprises steps of:

providing a solution comprising mRNA, wherein said solution optionally comprises a dispersant;

adding one or more agents that promote precipitation of mRNA, thereby obtaining a slurry (e.g., the one or more agents that promote precipitation of mRNA comprise an alcohol such as ethanol and/or a chaotropic salt such as guanidine thioisocyanate), wherein said adding optionally occurs in a Nutsche Filter or a stirred cell and wherein a dispersant is optionally added;

stirring a slurry prior to and/or while providing pressure to a slurry and/or a vacuum to the slurry sufficient to direct a slurry's mother liquor through a filter, thereby obtaining a precipitate-containing composition;

optionally drying the precipitate-containing composition (e.g., by continuing to provide pressure and/or vacuum such that precipitated mRNA is obtained as a cake;

optionally solubilizing a purified mRNA precipitate (e.g., a precipitate-containing composition or a dried cake) in an aqueous medium, thereby obtaining a solution comprising purified mRNA.

Thus, in some embodiments, the slurry comprises at least one dispersant. Examples of dispersants include and are not limited to one or more of ash, clay, diatomaceous earth, filtering agent, glass beads, plastic beads, polymers, polypropylene beads, polystyrene beads, salts (e.g., cellulose salts), sand, and sugars. The method may further include a step of drying the purified mRNA precipitate which is included in a cake along with the dispersant. The method may further include one or more steps for separating the dispersant from the purified mRNA precipitate, e.g., washing and drying the cake. The method may further include a step of solubilizing and eluting the purified mRNA from the cake using an aqueous medium, e.g., water, while filtering the dispersant.

Stirring Apparatuses Including Nutsche Filters and Stirred Cells

Any apparatus that provides agitation (e.g., stirring) of a contained liquid or slurry and can provide pressure and/or vacuum to the contained liquid or slurry may be used in the present invention.

An example of an apparatus suitable in the present invention is a Nutsche filter, e.g., an agitated Nutsche filter dryer (ANFD). Such Nutsche filters are well-known in the art. See, e.g., DE19917558A1, EP828978A4, JP03930616B2, JP2004167345A, KR1693166B1, U.S.20090065435A1, U.S.20090148384A1, U.S.20090292109A1, U.S.20110195166A1, U.S.20120165500A1, U.S. Pat. No. 5,139,667A, U.S. Pat. No. 5,544,425A, U.S. Pat. No. 5,659,971A, U.S. Pat. No. 7,494,794B2, U.S. Pat. No. 7,709,240B2, U.S. Pat. No. 7,871,805B2, WO2002092642A1, WO2003002230A1, and WO2008078646A1, each of which is incorporated herein by reference in its entirety.

A Nutsche filter used in any of the methods described herein can feature a variety of filter pore sizes and types. For example, a Nutsche filter can have an average pore size of about 0.01 micron to about 200 microns, about 1 micron to about 2000 microns, about 0.2 microns to about 5 micron, or about one micron to about 3 microns. In embodiments, an average pore size is about 0.5 micron or greater, about 0.75 micron or greater, about 1 micron or greater, about 2 microns or greater, about 3 microns or greater, about 4 microns or greater, or about 5 microns or greater. Methods herein can accommodate a variety of filter pore sizes while still retaining mRNA and without fouling a filter.

Another apparatus suitable in the present invention is an Amicon® Stirred Cell.

Other apparatuses, e.g., vessels, cells, and containers, which include, at least, a stirring means, a means for providing pressure and/or vacuum to a composition and/or slurry, and a means for filtering a composition and/or slurry may be used in the present invention.

Features/advantages of the apparatuses used herein include and are not limited to: vacuum and/or pressure filtration; minimal contamination of the cake; slurry contents can be kept fluidized until most of the mother liquor is filtered through; the filter's agitator can be used to maintain a smooth and uniform cake; the cake (e.g., a dry cake) can be washed after filtration by re-slurrying the cake; after washing, the mother liquor can be re-filtered and the cake can then be discharged by lowering the agitator and rotating it in such a manner that it brings all the cake towards the discharge port; it allows contained discharging and sampling; inert gas atmosphere can be maintained; very high solvent recovery; solvents are in closed systems, so no toxic vapors are let off in the atmosphere; personal safety is maintained and heat transfer surfaces can be provided to maintain filtration temperature; controlled heating and cooling by an integrated component or an external component (e.g., jacket); and considerable saving in manpower. An apparatus used herein allows many operations or steps required in the purification of large quantities of mRNA for therapeutic uses to take place within a single apparatus.

An apparatus described above may be used in the below-described methods and to produce the below-described compositions.

Compositions and Methods for their Production

The present invention provides methods for producing a composition enriched with full-length mRNA molecules which are greater than 500 nucleotides in length and encoding for a peptide or polypeptide of interest. The present invention also provides methods for producing a therapeutic composition enriched with full-length mRNA molecules encoding a peptide or polypeptide of interest for use in the delivery to or treatment of a subject, e.g., a human subject or a cell of a human subject or a cell that is treated and delivered to a human subject.

Accordingly, in certain embodiments the present invention provides a method for producing a therapeutic composition enriched with full-length mRNA that encodes a peptide or polypeptide for use in the delivery to or treatment of the lung of a subject or a lung cell. In certain embodiments the present invention provides a method for producing a therapeutic composition enriched with full-length mRNA that encodes for cystic fibrosis transmembrane conductance regulator (CFTR) protein. In certain embodiments the present invention provides a method for producing a therapeutic composition enriched with full-length mRNA that encodes for ATP-binding cassette sub-family A member 3 protein. In certain embodiments the present invention provides a method for producing a therapeutic composition enriched with full-length mRNA that encodes for dynein axonemal intermediate chain 1 protein. In certain embodiments the present invention provides a method for producing a therapeutic composition enriched with full-length mRNA that encodes for dynein axonemal heavy chain 5 (DNAH5) protein. In certain embodiments the present invention provides a method for producing a therapeutic composition enriched with full-length mRNA that encodes for alpha-1-antitrypsin protein. In certain embodiments the present invention provides a method for producing a therapeutic composition enriched with full-length mRNA that encodes for forkhead box P3 (FOXP3) protein. In certain embodiments the present invention provides a method for producing a therapeutic composition enriched with full-length mRNA that encodes one or more surfactant protein, e.g., one or more of surfactant A protein, surfactant B protein, surfactant C protein, and surfactant D protein.

In certain embodiments the present invention provides a method for producing a therapeutic composition enriched with full-length mRNA that encodes a peptide or polypeptide for use in the delivery to or treatment of the liver of a subject or a liver cell. Such peptides and polypeptides can include those associated with a urea cycle disorder, associated with a lysosomal storage disorder, with a glycogen storage disorder, associated with an amino acid metabolism disorder, associated with a lipid metabolism or fibrotic disorder, associated with methylmalonic acidemia, or associated with any other metabolic disorder for which delivery to or treatment of the liver or a liver cell with enriched full-length mRNA provides therapeutic benefit.

In certain embodiments the present invention provides a method for producing a therapeutic composition enriched with full-length mRNA that encodes for a protein associated with a urea cycle disorder. In certain embodiments the present invention provides a method for producing a therapeutic composition enriched with full-length mRNA that encodes for ornithine transcarbamylase (OTC) protein. In certain embodiments the present invention provides a method for producing a therapeutic composition enriched with full-length mRNA that encodes for arginosuccinate synthetase 1 protein. In certain embodiments the present invention provides a method for producing a therapeutic composition enriched with full-length mRNA that encodes for carbamoyl phosphate synthetase I protein. In certain embodiments the present invention provides a method for producing a therapeutic composition enriched with full-length mRNA that encodes for arginosuccinate lyase protein. In certain embodiments the present invention provides a method for producing a therapeutic composition enriched with full-length mRNA that encodes for arginase protein.

In certain embodiments the present invention provides a method for producing a therapeutic composition enriched with full-length mRNA that encodes for a protein associated with a lysosomal storage disorder. In certain embodiments the present invention provides a method for producing a therapeutic composition enriched with full-length mRNA that encodes for alpha galactosidase protein. In certain embodiments the present invention provides a method for producing a therapeutic composition enriched with full-length mRNA that encodes for glucocerebrosidase protein. In certain embodiments the present invention provides a method for producing a therapeutic composition enriched with full-length mRNA that encodes for iduronate-2-sulfatase protein. In certain embodiments the present invention provides a method for producing a therapeutic composition enriched with full-length mRNA that encodes for iduronidase protein. In certain embodiments the present invention provides a method for producing a therapeutic composition enriched with full-length mRNA that encodes for N-acetyl-alpha-D-glucosaminidase protein. In certain embodiments the present invention provides a method for producing a therapeutic composition enriched with full-length mRNA that encodes for heparan N-sulfatase protein. In certain embodiments the present invention provides a method for producing a therapeutic composition enriched with full-length mRNA that encodes for galactosamine-6 sulfatase protein. In certain embodiments the present invention provides a method for producing a therapeutic composition enriched with full-length mRNA that encodes for beta-galactosidase protein. In certain embodiments the present invention provides a method for producing a therapeutic composition enriched with full-length mRNA that encodes for lysosomal lipase protein. In certain embodiments the present invention provides a method for producing a therapeutic composition enriched with full-length mRNA that encodes for arylsulfatase B (N-acetylgalactosamine-4-sulfatase) protein. In certain embodiments the present invention provides a method for producing a therapeutic composition enriched with full-length mRNA that encodes for transcription factor EB (TFEB).

In certain embodiments the present invention provides a method for producing a therapeutic composition enriched with full-length mRNA that encodes for a protein associated with a glycogen storage disorder. In certain embodiments the present invention provides a method for producing a therapeutic composition enriched with full-length mRNA that encodes for acid alpha-glucosidase protein. In certain embodiments the present invention provides a method for producing a therapeutic composition enriched with full-length mRNA that encodes for glucose-6-phosphatase (G6PC) protein. In certain embodiments the present invention provides a method for producing a therapeutic composition enriched with full-length mRNA that encodes for liver glycogen phosphorylase protein. In certain embodiments the present invention provides a method for producing a therapeutic composition enriched with full-length mRNA that encodes for muscle phosphoglycerate mutase protein. In certain embodiments the present invention provides a method for producing a therapeutic composition enriched with full-length mRNA that encodes for glycogen debranching enzyme.

In certain embodiments the present invention provides a method for producing a therapeutic composition enriched with full-length mRNA that encodes for a protein associated with amino acid metabolism. In certain embodiments the present invention provides a method for producing a therapeutic composition enriched with full-length mRNA that encodes for phenylalanine hydroxylase enzyme. In certain embodiments the present invention provides a method for producing a therapeutic composition enriched with full-length mRNA that encodes for glutaryl-CoA dehydrogenase enzyme. In certain embodiments the present invention provides a method for producing a therapeutic composition enriched with full-length mRNA that encodes for propionyl-CoA caboxylase enzyme. In certain embodiments the present invention provides a method for producing a therapeutic composition enriched with full-length mRNA that encodes for oxalase alanine-glyoxylate aminotransferase enzyme.

In certain embodiments the present invention provides a method for producing a therapeutic composition enriched with full-length mRNA that encodes for a protein associated with a lipid metabolism or fibrotic disorder. In certain embodiments the present invention provides a method for producing a therapeutic composition enriched with full-length mRNA that encodes for a mTOR inhibitor. In certain embodiments the present invention provides a method for producing a therapeutic composition enriched with full-length mRNA that encodes for ATPase phospholipid transporting 8B1 (ATP8B1) protein. In certain embodiments the present invention provides a method for producing a therapeutic composition enriched with full-length mRNA that encodes for one or more NF-kappa B inhibitors, such as one or more of I-kappa B alpha, interferon-related development regulator 1 (IFRD1), and Sirtuin 1 (SIRT1). In certain embodiments the present invention provides a method for producing a therapeutic composition enriched with full-length mRNA that encodes for PPAR-gamma protein or an active variant.

In certain embodiments the present invention provides a method for producing a therapeutic composition enriched with full-length mRNA that encodes for a protein associated with methylmalonic acidemia. For example, in certain embodiments the present invention provides a method for producing a therapeutic composition enriched with full-length mRNA that encodes for methylmalonyl CoA mutase protein. In certain embodiments the present invention provides a method for producing a therapeutic composition enriched with full-length mRNA that encodes for methylmalonyl CoA epimerase protein.

In certain embodiments the present invention provides a method for producing a therapeutic composition enriched with full-length mRNA for which delivery to or treatment of the liver can provide therapeutic benefit. In certain embodiments the present invention provides a method for producing a therapeutic composition enriched with full-length mRNA that encodes for ATP7B protein, also known as Wilson disease protein. In certain embodiments the present invention provides a method for producing a therapeutic composition enriched with full-length mRNA that encodes for porphobilinogen deaminase enzyme. In certain embodiments the present invention provides a method for producing a therapeutic composition enriched with full-length mRNA that encodes for one or clotting enzymes, such as Factor VIII, Factor IX, Factor VII, and Factor X. In certain embodiments the present invention provides a method for producing a therapeutic composition enriched with full-length mRNA that encodes for human hemochromatosis (HFE) protein.

In certain embodiments the present invention provides a method for producing a therapeutic composition enriched with full-length mRNA that encodes a peptide or polypeptide for use in the delivery to or treatment of the cardiovasculature of a subject or a cardiovascular cell. In certain embodiments the present invention provides a method for producing a therapeutic composition enriched with full-length mRNA that encodes for vascular endothelial growth factor A protein. In certain embodiments the present invention provides a method for producing a therapeutic composition enriched with full-length mRNA that encodes for relaxin protein. In certain embodiments the present invention provides a method for producing a therapeutic composition enriched with full-length mRNA that encodes for bone morphogenetic protein-9 protein. In certain embodiments the present invention provides a method for producing a therapeutic composition enriched with full-length mRNA that encodes for bone morphogenetic protein-2 receptor protein.

In certain embodiments the present invention provides a method for producing a therapeutic composition enriched with full-length mRNA that encodes a peptide or polypeptide for use in the delivery to or treatment of the muscle of a subject or a muscle cell. In certain embodiments the present invention provides a method for producing a therapeutic composition enriched with full-length mRNA that encodes for dystrophin protein. In certain embodiments the present invention provides a method for producing a therapeutic composition enriched with full-length mRNA that encodes for frataxin protein. In certain embodiments the present invention provides a method for producing a therapeutic composition enriched with full-length mRNA that encodes a peptide or polypeptide for use in the delivery to or treatment of the cardiac muscle of a subject or a cardiac muscle cell. In certain embodiments the present invention provides a method for producing a therapeutic composition enriched with full-length mRNA that encodes for a protein that modulates one or both of a potassium channel and a sodium channel in muscle tissue or in a muscle cell. In certain embodiments the present invention provides a method for producing a therapeutic composition enriched with full-length mRNA that encodes for a protein that modulates a Kv7.1 channel in muscle tissue or in a muscle cell. In certain embodiments the present invention provides a method for producing a therapeutic composition enriched with full-length mRNA that encodes for a protein that modulates a Nav1.5 channel in muscle tissue or in a muscle cell.

In certain embodiments the present invention provides a method for producing a therapeutic composition enriched with full-length mRNA that encodes a peptide or polypeptide for use in the delivery to or treatment of the nervous system of a subject or a nervous system cell. For example, in certain embodiments the present invention provides a method for producing a therapeutic composition enriched with full-length mRNA that encodes for survival motor neuron 1 protein. For example, in certain embodiments the present invention provides a method for producing a therapeutic composition enriched with full-length mRNA that encodes for survival motor neuron 2 protein. In certain embodiments the present invention provides a method for producing a therapeutic composition enriched with full-length mRNA that encodes for frataxin protein. In certain embodiments the present invention provides a method for producing a therapeutic composition enriched with full-length mRNA that encodes for ATP binding cassette sub-family D member 1 (ABCD1) protein. In certain embodiments the present invention provides a method for producing a therapeutic composition enriched with full-length mRNA that encodes for CLN3 protein.

In certain embodiments the present invention provides a method for producing a therapeutic composition enriched with full-length mRNA that encodes a peptide or polypeptide for use in the delivery to or treatment of the blood or bone marrow of a subject or a blood or bone marrow cell. In certain embodiments the present invention provides a method for producing a therapeutic composition enriched with full-length mRNA that encodes for beta globin protein. In certain embodiments the present invention provides a method for producing a therapeutic composition enriched with full-length mRNA that encodes for Bruton's tyrosine kinase protein. In certain embodiments the present invention provides a method for producing a therapeutic composition enriched with full-length mRNA that encodes for one or clotting enzymes, such as Factor VIII, Factor IX, Factor VII, and Factor X.

In certain embodiments the present invention provides a method for producing a therapeutic composition enriched with full-length mRNA that encodes a peptide or polypeptide for use in the delivery to or treatment of the kidney of a subject or a kidney cell. In certain embodiments the present invention provides a method for producing a therapeutic composition enriched with full-length mRNA that encodes for collagen type IV alpha 5 chain (COL4A5) protein.

In certain embodiments the present invention provides a method for producing a therapeutic composition enriched with full-length mRNA that encodes a peptide or polypeptide for use in the delivery to or treatment of the eye of a subject or an eye cell. In certain embodiments the present invention provides a method for producing a therapeutic composition enriched with full-length mRNA that encodes for ATP-binding cassette sub-family A member 4 (ABCA4) protein. In certain embodiments the present invention provides a method for producing a therapeutic composition enriched with full-length mRNA that encodes for retinoschisin protein. In certain embodiments the present invention provides a method for producing a therapeutic composition enriched with full-length mRNA that encodes for retinal pigment epithelium-specific 65 kDa (RPE65) protein. In certain embodiments the present invention provides a method for producing a therapeutic composition enriched with full-length mRNA that encodes for centrosomal protein of 290 kDa (CEP290).

In certain embodiments the present invention provides a method for producing a therapeutic composition enriched with full-length mRNA that encodes a peptide or polypeptide for use in the delivery of or treatment with a vaccine for a subject or a cell of a subject. For example, in certain embodiments the present invention provides a method for producing a therapeutic composition enriched with full-length mRNA that encodes for an antigen from an infectious agent, such as a virus. In certain embodiments the present invention provides a method for producing a therapeutic composition enriched with full-length mRNA that encodes for an antigen from influenza virus. In certain embodiments the present invention provides a method for producing a therapeutic composition enriched with full-length mRNA that encodes for an antigen from respiratory syncytial virus. In certain embodiments the present invention provides a method for producing a therapeutic composition enriched with full-length mRNA that encodes for an antigen from rabies virus. In certain embodiments the present invention provides a method for producing a therapeutic composition enriched with full-length mRNA that encodes for an antigen from cytomegalovirus. In certain embodiments the present invention provides a method for producing a therapeutic composition enriched with full-length mRNA that encodes for an antigen from rotavirus. In certain embodiments the present invention provides a method for producing a therapeutic composition enriched with full-length mRNA that encodes for an antigen from a hepatitis virus, such as hepatitis A virus, hepatitis B virus, or hepatis C virus. In certain embodiments the present invention provides a method for producing a therapeutic composition enriched with full-length mRNA that encodes for an antigen from human papillomavirus. In certain embodiments the present invention provides a method for producing a therapeutic composition enriched with full-length mRNA that encodes for an antigen from a herpes simplex virus, such as herpes simplex virus 1 or herpes simplex virus 2. In certain embodiments the present invention provides a method for producing a therapeutic composition enriched with full-length mRNA that encodes for an antigen from a human immunodeficiency virus, such as human immunodeficiency virus type 1 or human immunodeficiency virus type 2. In certain embodiments the present invention provides a method for producing a therapeutic composition enriched with full-length mRNA that encodes for an antigen from a human metapneumovirus. In certain embodiments the present invention provides a method for producing a therapeutic composition enriched with full-length mRNA that encodes for an antigen from a human parainfluenza virus, such as human parainfluenza virus type 1, human parainfluenza virus type 2, or human parainfluenza virus type 3. In certain embodiments the present invention provides a method for producing a therapeutic composition enriched with full-length mRNA that encodes for an antigen from malaria virus. In certain embodiments the present invention provides a method for producing a therapeutic composition enriched with full-length mRNA that encodes for an antigen from zika virus. In certain embodiments the present invention provides a method for producing a therapeutic composition enriched with full-length mRNA that encodes for an antigen from chikungunya virus.

In certain embodiments the present invention provides a method for producing a therapeutic composition enriched with full-length mRNA that encodes for an antigen associated with a cancer of a subject or identified from a cancer cell of a subject. In certain embodiments the present invention provides a method for producing a therapeutic composition enriched with full-length mRNA that encodes for an antigen determined from a subject's own cancer cell, i.e., to provide a personalized cancer vaccine. In certain embodiments the present invention provides a method for producing a therapeutic composition enriched with full-length mRNA that encodes for an antigen expressed from a mutant KRAS gene.

In certain embodiments the present invention provides a method for producing a therapeutic composition enriched with full-length mRNA that encodes for an antibody. In certain embodiments, the antibody can be a bi-specific antibody. In certain embodiments, the antibody can be part of a fusion protein. In certain embodiments the present invention provides a method for producing a therapeutic composition enriched with full-length mRNA that encodes for an antibody to OX40. In certain embodiments the present invention provides a method for producing a therapeutic composition enriched with full-length mRNA that encodes for an antibody to VEGF. In certain embodiments the present invention provides a method for producing a therapeutic composition enriched with full-length mRNA that encodes for an antibody to tissue necrosis factor alpha. In certain embodiments the present invention provides a method for producing a therapeutic composition enriched with full-length mRNA that encodes for an antibody to CD3. In certain embodiments the present invention provides a method for producing a therapeutic composition enriched with full-length mRNA that encodes for an antibody to CD19.

In certain embodiments the present invention provides a method for producing a therapeutic composition enriched with full-length mRNA that encodes for an immunomodulator. In certain embodiments the present invention provides a method for producing a therapeutic composition enriched with full-length mRNA that encodes for Interleukin 12. In certain embodiments the present invention provides a method for producing a therapeutic composition enriched with full-length mRNA that encodes for Interleukin 23. In certain embodiments the present invention provides a method for producing a therapeutic composition enriched with full-length mRNA that encodes for Interleukin 36 gamma. In certain embodiments the present invention provides a method for producing a therapeutic composition enriched with full-length mRNA that encodes for a constitutively active variant of one or more stimulator of interferon genes (STING) proteins.

In certain embodiments the present invention provides a method for producing a therapeutic composition enriched with full-length mRNA that encodes for an endonuclease. In certain embodiments the present invention provides a method for producing a therapeutic composition enriched with full-length mRNA that encodes for an RNA-guided DNA endonuclease protein, such as Cas 9 protein. In certain embodiments the present invention provides a method for producing a therapeutic composition enriched with full-length mRNA that encodes for a meganuclease protein. In certain embodiments the present invention provides a method for producing a therapeutic composition enriched with full-length mRNA that encodes for a transcription activator-like effector nuclease protein. In certain embodiments the present invention provides a method for producing a therapeutic composition enriched with full-length mRNA that encodes for a zinc finger nuclease protein.

Synthesis, Including Large Scale-Synthesis of mRNA mRNAs according to the present invention may be synthesized according to any of a variety of known methods. For example, mRNAs according to the present invention may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7 or SP6 RNA polymerase), DNAse I, pyrophosphatase, and/or RNAse inhibitor. The exact conditions will vary according to the specific application. The presence of these reagents is undesirable in the final product according to several embodiments and may thus be referred to as impurities and a preparation containing one or more of these impurities may be referred to as an impure preparation. In some embodiments, the in vitro transcribing occurs in a single batch.

In one aspect, the method includes a step of transcribing in vitro, from one or more target DNA molecules with enzymes including RNA polymerases (e.g., SP6 or T7), purified mRNA molecules in which at least 80% of the purified mRNA molecules are full-length mRNA molecules. The method produces a composition including at least 100 mg of mRNA that is enriched for full-length mRNA.

In another aspect of the present invention is a method for large-scale production of full-length mRNA molecules. The method includes a step of transcribing in vitro, from a single batch of one or more target DNA molecules with enzymes including RNA polymerases (e.g., SP6 or T7), purified mRNA molecules that are greater than 500 nucleotides in length. At least 80% of the purified mRNA molecules are full-length mRNA molecules. The large-scale production produces at least 100 mg of mRNA in a single batch.

In another aspect of the present invention is a method for large-scale production of full-length mRNA molecules. The method includes a step of transcribing in vitro, from a single batch of one or more target DNA molecules with enzymes including RNA polymerases (e.g., SP6 or T7), purified mRNA molecules enriched with full-length mRNA molecules encoding a peptide or polypeptide of interest for use in the delivery to or treatment of a subject, e.g., a human subject or a cell of a human subject or a cell that is treated and delivered to a human subject, with at least 80% of the purified mRNA molecules being full-length mRNA molecules. The large-scale production produces at least 100 mg of mRNA in a single batch. In embodiments, at least 90% of the purified mRNA molecules being full-length mRNA molecules. In embodiments, the purified mRNA molecules encode a peptide or polypeptide as described above.

Yet another aspect of the present invention is a method for producing a composition enriched for full-length polypeptides. In embodiments, a method includes a step of transcribing in vitro in a single batch at least one target DNA molecule with an RNA polymerase (e.g., SP6 or T7) to produce at least 100 mg of mRNA molecules that are greater than 500 nucleotides in length; at least 80% of the mRNA molecules are full-length mRNA molecules. The method further includes a step of translating the mRNA molecules to produce a composition enriched for full-length polypeptides.

In some embodiments, at least 81%, 82%, 83%, 84%, 85%, 86%, 87%, 88%, 89%, 90%, 91%, 92%, 93%, 94%, 95%, 96%, 97%, 98%, 99%, 99.01%, 99.05%, 99.1%, 99.2%, 99.3%, 99.4%, 99.5%, 99.6%, 99.7%, 99.8%, 99.9% of the purified mRNA molecules are full-length mRNA molecules.

In some embodiments, a composition or a batch includes at least 200 mg, 300 mg, 400 mg, 500 mg, 600 mg, 700 mg, 800 mg, 900 mg, 1 g, 5 g, 10 g, 25 g, 50 g, 75 g, 100 g, 250 g, 500 g, 750 g, 1 kg, 5 kg, 10 kg, 50 kg, 100 kg, 1000 kg, or more mRNA.

In some embodiments, the mRNA molecules are greater than 600, 700, 800, 900, 1000, 2000, 3000, 4000, 5000, 10,000 or more nucleotides in length; also included in the present invention is mRNA having any length in between.

In some embodiments, a composition provides an increased quantity, e.g., at least two-fold, three-fold, four-fold, five-fold, or more, of full-length polypeptides relative to a composition having a lower percentage of full-length mRNA molecules.

In some embodiments, a composition provides an increased activity, e.g., at least two-fold, three-fold, four-fold, five-fold, or more, of translated polypeptides relative to a composition having a lower percentage of full-length mRNA molecules.

In some embodiments, a composition or a batch is prepared without a step of specifically removing mRNA molecules that are not full-length mRNA molecules.

In some embodiments, the DNA sequence to be transcribed may be optimized to facilitate more efficient transcription and/or translation. For example, the DNA sequence may be optimized regarding cis-regulatory elements (e.g., TATA box, termination signals, and protein binding sites), artificial recombination sites, chi sites, CpG dinucleotide content, negative CpG islands, GC content, polymerase slippage sites, and/or other elements relevant to transcription; the DNA sequence may be optimized regarding cryptic splice sites, or to provide mRNA secondary structure, stable free energy of mRNA, repetitive sequences, an mRNA stability motif, and/or other elements relevant to mRNA processing and stability; the DNA sequence may be optimized regarding codon usage bias, codon adaptability, internal chi sites, ribosomal binding sites (e.g., IRES), premature polyA sites, Shine-Dalgarno (SD) sequences, and/or other elements relevant to translation; and/or the DNA sequence may be optimized regarding codon context, codon-anticodon interaction, translational pause sites, and/or other elements relevant to protein folding. Optimization methods known in the art may be used in the present invention, e.g., GeneOptimizer by ThermoFisher and OptimumGene™, which is described in US 20110081708, the contents of which are incorporated herein by reference in its entirety.

In some embodiments, the DNA template includes a 5' and/or 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length. In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer.

In some embodiments, the purified mRNA includes a 5' untranslated region. In some embodiments, the purified mRNA includes a 3' untranslated region. In some embodiments, the purified mRNA includes a 5' untranslated region and a 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length. In some embodiments, a 5' untranslated region may be between about 10 and 50 nucleotides in length. In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length. In some embodiments, a 5' untranslated region may be between about 10 and 50 nucleotides in length.

Exemplary 3' and/or 5' UTR sequences can be derived from mRNA molecules which are stable (e.g., globin, actin, GAPDH, tubulin, histone, and citric acid cycle enzymes) to increase the stability of the sense mRNA molecule. For example, a 5' UTR sequence may include a partial sequence of a CMV immediate-early 1 (IE1) gene, or a fragment thereof to improve the nuclease resistance and/or improve the half-life of the polynucleotide. Also contemplated is the inclusion of a sequence encoding human growth hormone (hGH), or a fragment thereof to the 3' end or untranslated region of the polynucleotide (e.g., mRNA) to further stabilize the polynucleotide. Generally, these modifications improve the stability and/or pharmacokinetic properties (e.g., half-life) of the polynucleotide relative to their unmodified counterparts, and include, for example modifications made to improve such polynucleotides' resistance to in vivo nuclease digestion.

In some embodiments, the purified mRNA includes a poly A tail. In some embodiments, the purified mRNA includes a 5' untranslated region, a 3' untranslated region and a polyA tail. In some embodiments, the polyA tail is between 50 and 200 nucleotides in length. In some embodiments, the poly A tail is 200 nucleotides or longer in length.

In some embodiments, the purified mRNA molecules are detected using blotting, capillary electrophoresis, chromatography, fluorescence, gel electrophoresis, HPLC, silver stain, spectroscopy, ultraviolet (UV), or UPLC, or a combination thereof. Other detection methods known in the art are included in the present invention.

In some embodiments, the purified mRNA molecules are detected using UV absorption spectroscopy with separation by capillary electrophoresis. In this embodiment, a composition or a batch provides a lower number of peaks, peaks with a narrower base, and/or taller peaks when detected using capillary electrophoresis relative to a composition or a batch having a lower percentage of full-length mRNA molecules. For example, the composition or the batch provides a lower number of peaks, peaks with a narrower base, and/or taller peaks when detected using capillary electrophoresis relative to a composition or a batch purified using alternative methods.

In some embodiments, a method further includes a step of adding a cap and/or adding a polyA tail to the purified mRNA or to the full-length mRNA.

In some embodiments, the in vitro transcribing occurs in a single batch.

mRNA Length

According to various embodiments, the present invention may be used to purify in vitro synthesized mRNA of a variety of lengths. In some embodiments, the present invention may be used to purify in vitro synthesized mRNA of at least 500 bases in length, or of or greater than about 1 kb, 1.5 kb, 2 kb, 2.5 kb, 3 kb, 3.5 kb, 4 kb, 4.5 kb, 5 kb 6 kb, 7 kb, 8 kb, 9 kb, 10 kb, 11 kb, 12 kb, 13 kb, 14 kb, 15 kb, or 20 kb in length. In some embodiments, the present invention may be used to purify in vitro synthesized mRNA ranging from about 0.5-20 kb, about 1-15 kb, about 1-10 kb, about 5-20 kb, about 5-15 kb, about 5-12 kb, about 5-10 kb, about 8-20 kb, or about 8-15 kb in length. For example, typical mRNAs may be about 1 kb to about 5 kb in length. More typically, the mRNA will have a length of about 1 kb to about 3 kb. However, in some embodiments, the mRNA in the composition of the invention is much longer (greater than about 20 kb). In some embodiments, one or more modifications are selected from one or more modified nucleotides or a modified sugar phosphate backbones. In some embodiments, the present invention may be used to purify in vitro synthesized mRNA that is unmodified.

Modified mRNA Nucleotides

In certain embodiments, mRNA nucleotides are modified to provide "modified mRNA." A modified mRNA according to the invention can thus include, for example, backbone modifications, sugar modifications or base modifications. In some embodiments, the mRNA includes a modified nucleotide analogue that is selected from the group consisting of 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydro-uracil, 2-thio-uracil, 4-thio-uracil, 5-carboxymethylaminomethyl-2-thio-uracil, 5-(carboxyhydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxyacetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, beta.-D-mannosyl-queosine, wybutoxosine, and phosphoramidates, phosphorothioates, peptide nucleotides, methylphosphonates, 7-deazaguanosine, 5-methylcytosine and inosine. The preparation of such analogues is known to a person skilled in the art e.g. from the U.S. Pat. No. 4,373,071, U.S. Pat. No. 4,401,796, U.S. Pat. No. 4,415,732, U.S. Pat. No. 4,458,066, U.S. Pat. No. 4,500,707, U.S. Pat. No. 4,668,777, U.S. Pat. No. 4,973,679, U.S. Pat. No. 5,047,524, U.S. Pat. No. 5,132,418, U.S. Pat. No. 5,153,319, U.S. Pat. Nos. 5,262,530 and 5,700,642, the disclosure of which is included here in its full scope by reference.

Typically, mRNA synthesis includes the addition of a "cap" on the N-terminal (5') end, and a "tail" on the C-terminal (3') end. The presence of the cap is important in providing resistance to nucleases found in most eukaryotic cells. The presence of a "tail" serves to protect the mRNA from exonuclease degradation.

In some embodiments, a method further includes a step of adding a cap and/or adding a polyA tail to the purified mRNA or to the full-length mRNA. Thus, in some embodiments, mRNAs include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp (5'(A,G (5')ppp(5')A and G(5')ppp(5')G.

While mRNA provided from in vitro transcription reactions may be desirable in some embodiments, other sources of mRNA are contemplated as within the scope of the invention including wild-type mRNA produced from bacteria, fungi, plants, and/or animals.

In some embodiments, mRNAs include a 5' and/or 3' untranslated region. In some embodiments, a 5' untranslated region includes one or more elements that affect an mRNA's stability or translation, for example, an iron responsive element. In some embodiments, a 5' untranslated region may be between about 10 and 50 nucleotides in length. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 10 and 50 nucleotides in length or longer. In some embodiments, a 3' untranslated region may be between 50 and 500 nucleotides in length or longer.

The present invention further includes a composition including a purified mRNA precipitate produced by an above aspect and/or embodiment.

The present invention further includes a pharmaceutical composition including a purified mRNA precipitate produced by an above aspect and/or embodiment and at least one pharmaceutically-acceptable excipient.

The present invention further includes a method for treating a disease or disorder comprising administering to a subject in need thereof a pharmaceutical composition of the above aspect and/or embodiment.

Any aspect or embodiment described herein can be combined with any other aspect or embodiment as disclosed herein. While the disclosure has been described in conjunction with the detailed description thereof, the above description is intended to illustrate and not limit the scope of the disclosure, which is defined by the scope of the appended claims. Other aspects, advantages, and modifications are within the scope of the following claims.

Additional teaching relevant to the present invention are described in one or more of the following: WO 2010/053572; WO 2011/068810; WO 2012/075040; WO 2012/170889; WO 2012/170930; WO 2013/063468; WO 2013/149140; WO 2013/149141; WO 2013/185067; WO 2013/185069; WO 2014/089486; WO 2014/152513; WO 2014/152659; WO 2014/152673; WO 2014/152774; WO 2014/152966; WO 2014/153052; WO 2015/061461; WO 2015/061467; WO 2015/061491; WO 2015/061500; WO 2015/148247; WO 2015/164773; WO 2015/184256; WO 2015/200465; WO 2016/004318; WO 2016/149508; WO/2014/152940; PCT/US16/57044; U.S. 62/320,073; U.S. 62/349,331; U.S. 62/420,413; U.S. 62/420,421; U.S. 62/420,428; U.S. 62/420,435; U.S. 62/421,007; U.S. 62/421,021, and the related applications filed Feb. 27, 2017 by Applicant entitled "LARGE SCALE SYNTHESIS OF MESSENGER RNA" (U.S. 62/464,043), "METHODS FOR PURIFICATION OF MESSENGER RNA" (U.S. 62/463,981), and "NOVEL CODON-OPTIMIZED CFTR MRNA" (U.S. 62/464,215), each of which is incorporated by reference in its entirety.

Although methods and materials similar or equivalent to those described herein can be used in the practice or testing of the present invention, suitable methods and materials are described below. All publications, patent applications, patents, and other references mentioned herein are incorporated by reference in its entirety. The references cited herein are not admitted to be prior art to the claimed invention. In addition, the materials, methods, and examples are illustrative only and are not intended to be limiting.

EXAMPLES

Example 1

The Present Invention, Using a Stirred Cell, can Purify 1 Gram of Intact mRNA that is Substantially Contaminant-Free In this example, in vitro transcribed mRNA was purified via a novel filtration method using an Amicon® stirred cell, which operates by separating a slurry from its mother liquor through a filtering screen or membrane in a closed system using pressure and/or vacuum.

1 gram of mRNA encoding for the Cystic Fibrosis Transmembrane Conductance Regulator protein (CFTR) was in vitro transcribed (IVT) using standard procedures. See, the related applications filed Feb. 27, 2017 by Applicants entitled "LARGE SCALE SYNTHESIS OF MESSENGER RNA" (U.S. 62/464,043) and "NOVEL CODON-OPTIMIZED CFTR MRNA" (U.S. 62/464,215), each of which is incorporated by reference in its entirety.

Briefly, for each gram of mRNA transcribed, a reaction containing 8 mg of a linearized double stranded DNA plasmid with an RNA polymerase-specific promoter, RNA polymerase, RNase inhibitor, pyrophosphatase, 29 mM NTPs, 10 mM DTT and a reaction buffer (10×-800 mM HEPES, 20 mM spirmidine, 250 mM MgCl, pH 7.7) was prepared and quantity sufficient (QS) to 179 ml with RNase-free water then incubated at 37° C. for 60 min The reaction was then quenched by the addition of DNase I and a DNase I buffer (10×-100 mM Tris-HCl, 5 mM $MgCl_2$ and 25 mM $CaCl_2$, pH 7.6) to facilitate digestion of the double-stranded DNA template in preparation for purification. The final reaction volume was 204 ml.

The mRNA produced in the transcription reaction was precipitated by first adding 2.3 volumes of GSCN buffer (4M guanidine thiocyanate, 25 mM sodium citrate pH 6.5, 0.5% N-lauroylsarcosine sodium salt) with stirring for five minutes via a magnetic stir bar, followed by adding 1.7 volumes ethanol with stirring for another five minutes to produce 1,200 ml of mRNA slurry.

In step #1 of Table 1, to a 400 ml Amicon® stirred cell, fitted with a 75 mm diameter 0.45 µM PVDF membrane, was added 400 ml of mRNA slurry, with stirring at 200 RPM. The cell was pressurized to 40 PSI and 350 ml passed through the filter.

Steps #2 to #4 of Table 1 were performed similarly until the entire 1,200 ml of mRNA slurry had been loaded and filtered. The mRNA precipitate was brought up to a volume of about 50 ml with 2.3:1.7 GSCN:ethanol.

The mRNA precipitate was washed four times (steps #5 to #8) with 2.3:1.7 GSCN:ethanol with stirring and under pressure (as shown) to filter the GSCN:ethanol wash solution. The washed mRNA precipitate was brought up to a volume of 50 ml with 80% ethanol.

Next, the product was washed eight times (steps #9 to #16) with 80% ethanol with stirring and under pressure.

TABLE 1 sequential load and wash steps for Amicon ® stirred cell

| Step | Load identity | Vol loaded (ml) | $N_2$ pressure (psi) | Vol passed through (ml) | Time (s) |
|---|---|---|---|---|---|
| 1 | Precipitate Slurry | 400 | 40 | 350 | 40 |
| 2 | Precipitate Slurry | 350 | 40 | 350 | 40 |
| 3 | Precipitate Slurry | 350 | 25 | 250 | 120 |
| 4 | Precipitate Slurry | 100 | 40 | 300 | 120 |
| 5 | 2.3:1.7 GSCN:Ethanol | 350 | 40 | 350 | 100 |
| 6 | 2.3:1.7 GSCN:Ethanol | 350 | 40 | 350 | 100 |
| 7 | 2.3:1.7 GSCN:Ethanol | 350 | 40 | 350 | 100 |
| 6 | 2.3:1.7 GSCN:Ethanol | 350 | 40 | 350 | 100 |
| 9 | 80% Ethanol | 350 | 40 | 350 | 60 |
| 10 | 80% Ethanol | 350 | 40 | 350 | 60 |
| 11 | 80% Ethanol | 350 | 40 | 350 | 60 |
| 12 | 80% Ethanol | 350 | 40 | 350 | 60 |
| 13 | 80% Ethanol | 350 | 40 | 350 | 60 |
| 14 | 80% Ethanol | 350 | 40 | 350 | 60 |
| 15 | 80% Ethanol | 350 | 40 | 350 | 60 |
| 16 | 80% Ethanol | 350 | 40 | 350 | 60 |

The ethanol-washed precipitate, i.e., purified mRNA, contained within the stirred cell was dissolved and eluted by addition of 350 ml water, yielding 750 mg mRNA.

An additional 350 ml water was added and eluted, yielding 100 mg more mRNA. The resulting mRNA was subsequently dialyzed into water to yield a pure mRNA solution.

Figure 2:
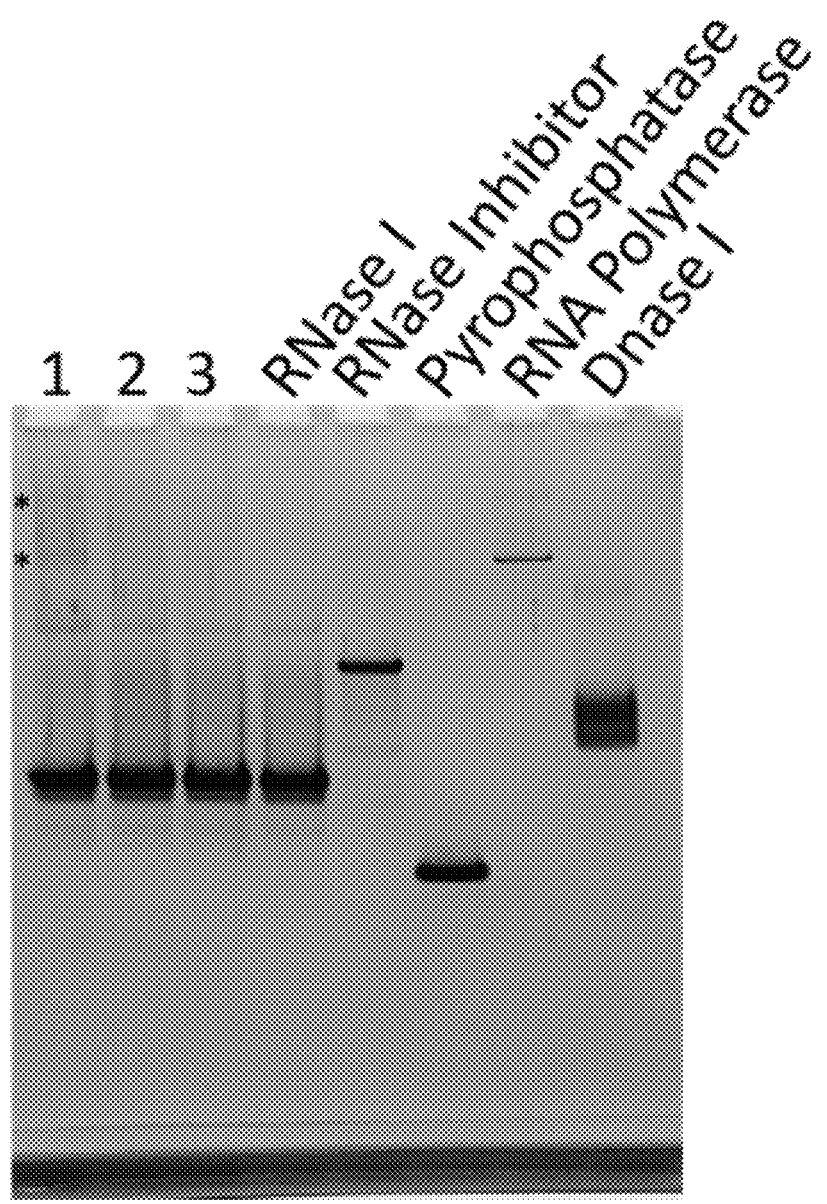
FIG. 2 is a digital image of a 10% SDS-PAGE stained with silver staining detecting residual enzymes in RNase I degraded mRNA samples. The image shows: lane 1: Representative engineering lot of CFTR mRNA+RNase I; lane 2: stirred-cell purified CFTR mRNA transcript+RNase I; lane 3: CFTR mRNA transcript purified with Nutsche filter using polystyrene beads+RNase I; and lanes 4 to 8: Component enzymes as labeled.

The pure mRNA was analyzed for integrity using TAE Agarose gel electrophoresis (FIG. 1, lane 2) and purity using SDS-PAGE with silver staining (FIG. 2, lane 2). These gels show intact, full-length mRNA products which are free of (detectable) contaminating proteins used in the IVT process.

The pure mRNA resulting from the present invention can be compared to mRNA purified using tangential flow filtration (TFF) (FIG. 2, lane 1). The mRNA purified using TFF shows trace levels of residual enzymes (marked with *). The integrity of the pure mRNA resulting from the present invention compares favorably to mRNA purified using a Qiagen® column (FIG. 1, lane 4).

These data show that the present invention is capable of producing pure, intact and full-length mRNA that has substantially no detectable contaminant enzymes used in the IVT process to produce the mRNA, as viewed by TAE Agarose gel electrophoresis or by SDS-PAGE with silver staining.

Example 2

Scaling up to 2.5 Grams of mRNA and Using a Nutsche Filter Results in Inefficient Purification In this example, the amount of in vitro transcribed mRNA scaled-up and filtered using a Nutsche filter, which has a larger volume than the Amicon® stirred cell used in Example 1. The Nutsche filer also operates by separating a slurry from its mother liquor through a filtering screen and membrane in a closed system using pressure and/or vacuum.

In this example, a five-liter Nutsche filter, which was outfitted with a motor-driven impeller and a 10 µm SS screen as a frit and a 150 mm 0.22 µm PVDF membrane, was used to purify 2.5 grams of previously-purified CFTR mRNA. The mRNA was precipitated by first adding a $\frac{1}{10}^{th}$ volume of 5M NaCl and 3 volumes of ethanol while stirring for 5 min with a magnetic stir bar to form a slurry.

In step #1 of Table 2, 4,000 ml of the slurry was added to the filter, while stirring. The filter was pressurized to 10 PSI with $N_2$, and clear buffer was collected through the filter outlet.

Steps #2 and #3 were performed similarly (except the pressure was raised to 40 PSI) until the entire eight liters of mRNA slurry had been loaded and filtered.

TABLE 2 sequential load and wash steps for Nutsche filter

| Step # | Load identity | Vol loaded (ml) | $N_2$ pressure (psi) | Vol passed through (ml) | Time (s) |
|---|---|---|---|---|---|
| 1 | Precipitate Slurry | 4000 | 10 | 3000 | 510 |
| 2 | Precipitate Slurry | 3000 | 40 | 1000 | 600 |
| 3 | Precipitate Slurry | 1000 | 40 | 2000 | 960 |

Unfortunately, the mother liquor flow rate decreased to the point that it was too slow to continue the experiment.

This example shows that it may be inefficient to simply scale up the volume of mRNA precipitant solution (i.e., slurry) since the greater amount of mRNA precipitant slows the rate of filtration.

Example 3

The Present Invention, Using a Nutsche Filter and Addition of a Dispersant, can Efficiently Purify 2.5 Gram of an mRNA Mixture to Provide an Intact mRNA that is Substantially Contaminant-Free In this example, in vitro transcribed mRNA prepared as described above was purified via a novel filtration method using a Nutsche filter, which operates by separating a slurry from its mother liquor through a filtering screen and membrane in a closed system using pressure and/or vacuum. However, unlike the method described in Example 2, a dispersant was added, which prevented precipitated mRNA from blocking the filter, which significantly slowed the rate of filtration.

Table 3 below provides an exemplary embodiment of this method.

In this example, a five-liter Nutsche filter, which was outfitted with a motor-driven impeller and a 1 μm SS screen as a frit, was used to purify 2.5 grams of previously-purified CFTR mRNA as previously described in U.S. 2015/0376220 A1 and/or U.S. 2016/0040154 A1, each of which is incorporated by reference in its entirety. 500 g of poly(styrene-co-divinylbenzene) microsphere beads (8.0-9.0 μm avg. particle size) was added as a dispersant to the 2.5 grams of mRNA.

The mRNA was precipitated by first adding 2.3 volumes of GSCN buffer (4M guanidine thiocyanate, 25 mM sodium citrate pH 6.5, 0.5% N-lauroylsarcosine sodium salt) with stirring for five minutes via a magnetic stir bar, followed by adding 1.7 volumes ethanol with stirring for another five minutes to produce 2,900 ml of precipitated mRNA-microsphere slurry. The slurry was added to the five-liter Nutsche filter. The filter was pressurized to 10 PSI with $N_2$ and 2,000 ml of clear buffer was collected through the filter outlet (step #1 of Table 3) resulting in a precipitated mRNA-microsphere cake.

The precipitated mRNA-microsphere cake was washed four times (steps #2 to #5) with 2.3:1.7 GSCN:ethanol with stirring and under pressure (as shown) to filter the GSCN:ethanol wash solution. The washed precipitated mRNA-microsphere cake was brought up to a volume of approximately 900 ml with 80% ethanol.

Next, the precipitated mRNA-microsphere cake was washed six times with 80% ethanol while stirring and under pressure (as shown in step #6 to #11). The ethanol washed cake was brought up to a volume of approximately 900 ml with 80% ethanol. On final wash, pressure was applied until all ethanol was pushed out of the cake, such that the cake was substantially dry.

TABLE 3 sequential load and wash steps for bead-assisted Nutsche filter

| # | Load identity | Vol loaded (ml) | $N_2$ pressure (psi) | Vol passed through (ml) | Time (s) |
|---|---|---|---|---|---|
| 1 | Precipitate Slurry | 2900 | 10 | 2000 | 200 |
| 2 | 2.3:1.7 GSCN:Ethanol | 2000 | 10 | 2000 | 280 |
| 3 | 2.3:1.7 GSCN:Ethanol | 2000 | 10 | 2000 | 283 |
| 4 | 2.3:1.7 GSCN:Ethanol | 2000 | 10 | 2000 | 230 |
| 5 | 2.3:1.7 GSCN:Ethanol | 2000 | 10 | 2000 | 250 |
| 6 | 80% Ethanol | 2000 | 10 | 2000 | 300 |
| 7 | 80% Ethanol | 2000 | 10 | 2000 | 350 |
| 8 | 80% Ethanol | 2000 | 10 | 2000 | 360 |
| 9 | 80% Ethanol | 2000 | 10 | 2000 | 405 |
| 10 | 80% Ethanol | 2000 | 20 | 2000 | 210 |
| 11 | 80% Ethanol | 2000 | 10 | 2900 | 410 |

The ethanol-washed, precipitated mRNA-microsphere cake contained within the stirred cell was dissolved and eluted by addition of 500 ml water, yielding 1.2 g mRNA. An additional 500 ml water was added and eluted, yielding 450 mg more mRNA. A third elution yielded 1.00 mg more mRNA.

Since the beads facilitated drying of the ethanol from the precipitated mRNA (in the cake), a further dialysis step was unnecessary to yield an aqueous solution of the mRNA.

The purified mRNA was analyzed for integrity using TAE Agarose gel electrophoresis (FIG. 1, lane 3) and purity using SDS-PAGE with silver staining (FIG. 2, lane 4). These gels show intact, full-length mRNA products which are free of (detectable) contaminating proteins used in the IVT process.

The purified mRNA resulting from the present invention may be compared to mRNA purified using TFF (FIG. 2, lane 1). The mRNA purified using TFF shows trace levels of residual enzymes (marked with *). The integrity of the pure mRNA resulting from the present invention compares favorably to mRNA purified using a Qiagen® column (FIG. 1, lane 4).

These data show that the present invention, when using a Nutsche filter and adding a dispersant, is particularly suitable for large-scale purification of mRNA as the invention is capable of producing large-scale pure, intact and full-length mRNA that has substantially no detectable contaminant enzymes used in the IVT process to produce the mRNA, as viewed by TAE Agarose gel electrophoresis or by SDS-PAGE with silver staining.

What is claimed is:

1. A method of large scale purification of mRNA, comprising steps of:
    providing a solution comprising at least 250 mg of in vitro synthesized mRNA;
    adding one or more agents that promote precipitation of the mRNA, thereby obtaining a slurry;
    stirring the slurry in an agitated filter dryer at a speed between 50 revolutions per minute RPM and 500 revolutions per minute underpressure to the slurry and/or a vacuum to the slurry sufficient to direct the slurry's mother liquor through the filter, thereby obtaining a precipitate-containing composition; and
    washing the precipitate-containing composition with stiffing and under pressure, thereby yielding a purified mRNA precipitate,
    wherein the purified mRNA has reduced impurity of enzyme reagents used in in vitro synthesis as compared to the otherwise same mRNA purified by tangential flow filtration and has an integrity greater than about 95% determined by sodium dodecyl sulfate polyacrylamide gel electrophoresis with silver staining.

2. The method of claim 1, wherein the method purifies at least about 2.5 grams mRNA in one batch.

3. The method of claim 1, wherein the pressure is between about 5 pounds per square inch and about 100 pounds per square inch.

4. The method of claim 1, further comprising adding one or more agents that denatures proteins and/or keeps proteins soluble in an aqueous medium.

5. The method of claim 1, further comprising a step of drying the purified mRNA precipitate, wherein the purified mRNA precipitate is dried by continuing to provide pressure and/or vacuum such that precipitated mRNA is obtained as a cake of precipitate.

6. The method of claim 1, wherein the slurry comprises at least one dispersant.

7. The method of claim 6, further comprising a step of drying the purified mRNA precipitate which is included in a cake along with the dispersant or comprising one or more steps for separating the dispersant from the purified mRNA precipitate.

8. The method of claim 1, wherein the one or more agents that promote precipitation of mRNA are a chaotropic salt and an alcohol.

9. The method of claim 1, wherein the mRNA is contacted with the one or more agents that promote precipitation of mRNA for a total amount of about one minute to about one hour.

10. The method of claim 1, further comprising a step of solubilizing the purified mRNA precipitate in an aqueous medium, thereby obtaining a solution comprising purified mRNA.

11. The method of claim 1, wherein the mRNA encodes cystic fibrosis transmembrane conductance regulator protein (CFTR).

12. The method of claim 1, wherein the mRNA encodes ornithine transcarbamylase (OTC).

13. A composition comprising a purified mRNA precipitate prepared by the method of claim 1.

14. A pharmaceutical composition comprising the composition of claim 13 and at least one pharmaceutically-acceptable excipient.

15. A method for treating a disease or disorder comprising administering to a subject in need thereof the pharmaceutical composition of claim 14.

16. The method of claim 1, wherein the method purifies at least 5 grams mRNA in one batch.

17. The method of claim 1, wherein the method purifies at least 10 grams mRNA in one batch.

18. The method of claim 1, wherein the total purified mRNA is recovered in an amount that results in a yield of at least about 80%.

19. The method of claim 1, wherein the total purified mRNA is recovered in an amount that results in a yield of at least about 95%.

20. The method of claim 1, wherein the purified mRNA has an integrity greater than about 98% determined by sodium dodecyl sulfate polyacrylamide gel electrophoresis with silver staining.

21. The method of claim 1, wherein the slurry comprises at least one filtration aid.

* * * * *

UNITED STATES PATENT AND TRADEMARK OFFICE
CERTIFICATE OF CORRECTION

PATENT NO. : 10,808,241 B2
APPLICATION NO. : 15/906864
DATED : October 20, 2020
INVENTOR(S) : Jonathan Abysalh et al.

Page 1 of 1

It is certified that error appears in the above-identified patent and that said Letters Patent is hereby corrected as shown below:

In the Claims

Column 40, Claim 1, Line 55, there should be a space inserted between the words "under" and "pressure".

Signed and Sealed this
Twentieth Day of July, 2021

Drew Hirshfeld
*Performing the Functions and Duties of the*
*Under Secretary of Commerce for Intellectual Property and*
*Director of the United States Patent and Trademark Office*